(12) United States Patent
Karanjikar et al.

(10) Patent No.: US 8,647,492 B2
(45) Date of Patent: *Feb. 11, 2014

(54) METHOD OF PRODUCING COUPLED RADICAL PRODUCTS FROM BIOMASS

(75) Inventors: Mukund Karanjikar, West Valley, UT (US); Sai Bhavaraju, West Jordan, UT (US); Ashok V. Joshi, Salt Lake City, UT (US); Pallavi Chitta, West Valley, UT (US); David Joel Hunt, Ogden, UT (US)

(73) Assignee: Ceramatec, Inc., Salt Lake City, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/840,913

(22) Filed: Jul. 21, 2010

(65) Prior Publication Data

US 2011/0027848 A1 Feb. 3, 2011

Related U.S. Application Data

(63) Continuation of application No. 12/840,508, filed on Jul. 21, 2010, now Pat. No. 8,506,789, which is a continuation of application No. 12/840,401, filed on Jul. 21, 2010.

(60) Provisional application No. 61/228,078, filed on Jul. 23, 2009, provisional application No. 61/258,557, filed on Nov. 5, 2009, provisional application No. 61/260,961, filed on Nov. 13, 2009.

(51) Int. Cl.
*C25B 3/10* (2006.01)
*C25B 3/00* (2006.01)

(52) U.S. Cl.
USPC .......................................... 205/462; 205/415

(58) Field of Classification Search
USPC ........... 585/240, 242, 310, 733; 205/462, 415
See application file for complete search history.

(56) References Cited

U.S. PATENT DOCUMENTS 2,760,926 A * 8/1956 Kronenthal .................... 205/455
2,867,569 A    1/1959 Kronenthal (Continued)

FOREIGN PATENT DOCUMENTS

JP       06271499 A *  9/1994 ............ C07C 53/126
SU          979325 A1 * 12/1982 .............. C07C 51/41
WO   WO 2007095215 A2 *  8/2007

OTHER PUBLICATIONS

Kobzeva et al., "Effect of a Solvent on Anode Processes During Electrolysis of Carboxylic Acids", Elektrokhimiya (no month, 1975), vol. 11, No. 5, pp. 718-724. 1 Page Abstract Only.*
Ono et al., "Electrolysis of Fatty Acids. I. Electrolysis of Fatty Acids of Camellia Oil", Nippon Kagaku Kaishi (1921-47) (no month, 1950), Ind. Chem. Sect. 53, pp. 359-361. 1 Page Abstract Only.*

(Continued)

*Primary Examiner* — Edna Wong
(74) *Attorney, Agent, or Firm* — David Fonda

(57) ABSTRACT

A method that produces coupled radical products from biomass. The method involves obtaining a lipid or carboxylic acid material from the biomass. This material may be a carboxylic acid, an ester of a carboxylic acid, a triglyceride of a carboxylic acid, or a metal salt of a carboxylic acid, or any other fatty acid derivative. This lipid material or carboxylic acid material is converted into an alkali metal salt. The alkali metal salt is then used in an anolyte as part of an electrolytic cell. The electrolytic cell may include an alkali ion conducting membrane (such as a NaSICON membrane). When the cell is operated, the alkali metal salt of the carboxylic acid decarboxylates and forms radicals. Such radicals are then bonded to other radicals, thereby producing a coupled radical product such as a hydrocarbon. The produced hydrocarbon may be, for example, saturated, unsaturated, branched, or unbranched, depending upon the starting material.

25 Claims, 9 Drawing Sheets

(56) References Cited

U.S. PATENT DOCUMENTS

| | | | |
|---|---|---|---|
| 3,994,471 A | | 11/1976 | Turolla |
| 4,006,065 A | * | 2/1977 | Meresz et al. ............ 205/462 |
| 4,123,336 A | | 10/1978 | Seko et al. |
| 4,402,804 A | | 9/1983 | Jackson |
| 4,464,236 A | | 8/1984 | Noding |
| 5,084,146 A | | 1/1992 | Huang |
| 5,290,405 A | * | 3/1994 | Joshi et al. ............ 205/338 |
| 5,580,430 A | | 12/1996 | Balagopal et al. |
| 5,633,400 A | | 5/1997 | Wagner et al. |
| 5,841,002 A | | 11/1998 | Harrison et al. |
| 5,892,107 A | | 4/1999 | Farone et al. |
| 6,238,543 B1 | | 5/2001 | Law et al. |
| 6,362,380 B1 | | 3/2002 | Eicken et al. |
| 6,392,091 B2 | | 5/2002 | Lin |
| 2001/0019020 A1 | * | 9/2001 | Merk et al. ............ 205/413 |
| 2005/0177008 A1 | | 8/2005 | Balagopal et al. |
| 2008/0177114 A1 | | 7/2008 | Goossen et al. |
| 2008/0245671 A1 | | 10/2008 | Balagopal et al. |
| 2009/0074611 A1 | | 3/2009 | Monzyk et al. |
| 2010/0159553 A1 | | 6/2010 | Bradin |
| 2010/0258447 A1 | | 10/2010 | Fan |
| 2010/0331170 A1 | | 12/2010 | Balagopal et al. |
| 2011/0024288 A1 | | 2/2011 | Bhavaraju et al. |
| 2011/0111475 A1 | * | 5/2011 | Kuhry et al. ............ 435/166 |
| 2011/0168569 A1 | | 7/2011 | Bhavaraju et al. |
| 2011/0226633 A1 | | 9/2011 | Bhavaraju et al. |
| 2012/0031769 A1 | | 2/2012 | Bhavaraju et al. |
| 2012/0123168 A1 | | 5/2012 | Bhavaraju |
| 2012/0142945 A1 | | 6/2012 | Hwang et al. |

OTHER PUBLICATIONS

Minami et al., "Electrolysis of Fatty Acids. II. Electrolysis of Oleic and Elaidic Acids", Kogyo Kagaku Zasshi (no month, 1950), vol. 53, pp. 391-393. 1 Page Abstract Only.*

Obermuller, "Saponification by Sodium Ethoxide", Zeitschrift fuer Physiologische Chemie, 16, 152-9 from J. Chem. Soc., Abstr. 62, 139-40, no month, 1892. 1 Page Abstract Only.*

Sekine, "Effect of the Concentration of Acetate or Propionate on the Abnormal Phenomena in the Kolbe Reaction", Denki Kagaku (no month, 1973), vol. 41, No. 9, pp. 702-707.*

Palit, "The Solubility of Soaps and of Some Salts in Mixtures of Solvents, One of Which is of Glycolic Type", J. of the American Chemical Society (Dec. 1947), vol. 69, No. 12, pp. 3120-3129.*

Conway et al., "New Approaches to the Study of Electrochemical Decarboxylation and the Kolbe Reaction. I. The Model Reaction with Formate", Canadian Journal of Chemistry (no month, 1963), vol. 41, pp. 21-37.*

Kang, Sang Yoon "PCT International Search Report", Int. App. No. PCT/US2010/042756, (Feb. 28, 2011),1-3.

Kang, Sang Yoon "PCT Written Opinion", Int. App. No. PCT/US2010/042756, (Feb. 28, 2011),1-4.

Park, Sang Ho "PCT International Search Report", Int. App. No. PCT/US2010/042715, (Apr. 29, 2011),1-3.

Park, Sang Ho "PCT Written Opinion", Int. App. No. PCT/US2010/042715, (Apr. 29, 2011),1-4.

Park, Sang Ho "PCT International Search Report", Int. App. No. PCT/US2010/042780, (May 2, 2011),1-3.

Park, Sang Ho "PCT Written Opinion", Int. App. No. PCT/US2010/042780, (May 2, 2011),1-5.

Bond, Jesse Q., et al., "Integrated Catalytic Conversion of gamma-Valerolactone of Liquid Alkenes for Transportation Fuels", Science, (Feb. 26, 2010),vol. 327: 1110-1114.

Bozell, Joseph J., "Connecting Biomass and Petroleum Processing with a Chemical Bridge", Science, (Jul. 30, 2010),vol. 329: 522-523.

Chum, H L., et al., "Photoelectrochemistry of Levulinic Acid on Undoped Platinized n-TIO2 Powders", J. Phys. Chem, (1983),vol. 87: 3089-3093.

Rabjohn, et al., "Kolbe Electrosynthesis of Alkanes with Multiple Quaternary Carbon Atoms", J. Org. Chem., (1981),vol. 46, pp. 4082-4083.

Schafer, Hans-Jurgen "Recent Contributions of Kolbe Electrolysis to Organic Synthesis", Topics in Current Chemistry, (1990),vol. 152: 91-151.

Wong, Edna "USPTO Office Action", U.S. Appl. No. 12/840,508, (Nov. 2, 2011),17 pages.

Palit, Santi R., "The Solubility of Soaps and of Some Salts in Mixtures of Solvents, One of Which Is of Glycolic Type", Utah Consortia UALC, vol. 69, (Dec. 1947),3120-29.

Wong, Edna "Non-Final Office Action", U.S. Appl. No. 12/840,508, (Apr. 26, 2012),1-32.

Mendez, Zulmariam "Non-Final Office Action", U.S. Appl. No. 12/840,401, (Jun. 5, 2012),1-12.

Wong, Edna "Non-Final Office Action", U.S. Appl. No. 13/357,463, (Jun. 4, 2012),1-25.

Pande, et al., "Studies on Kolbe's Electrosynthesis", Electrochimica Acta, Aug. 1961, vol. 4, (Aug. 1961),215-231.

Ho, Park S., "International Search Report", PCT US 2011/035782 (corresponding to U.S. Appl. No. 13/103,716, (Feb. 9, 2012),1-3

Ho, Park S., "Written Opinion of the International Searching Authority", PCT US 2011/035782 (corresponding to U.S. Appl. No. 13/103,716, (Feb. 9, 2012),1-4.

Choi, et al., "Recovery of lactic acid from sodium lactate by ion substitution using ion-exchange membrane", Separation and Purification Technology 28 (2002), Elsevier, (Mar. 4, 2002),69-79.

Habova, et al., "Application of Electrodialysis for Lactic Acid Recovery", Czech J. Food Sci., vol. 19, No. 2 (2001), (Jan. 1, 2001),73-80.

Huang, et al., "Application of electrodialysis to the production of organic acids: State-of-the-art and recent developments", Journal of Membrane Science 288 (2007), Elsevier, (Nov. 25, 2006),1-12.

Lu, et al., "Modeling of the mass transfer and conduction behavior in electro-electrodialysis with oil/water emulsion as the catholyte", Journal of Membrane Science 322 (2008), Elsevier, (Jun. 5, 2008),265-274.

Moon, et al., "Competitive Anion Transport in Desalting Mixtures of Organic Acids by Batch Electrodialysis", Journal of Membrane Science 141 (1998), Elsevier, (Apr. 1, 1998),75-89.

Palaty, et al., "Continuous dialysis of carboxylic acids. Permeability of Neosepta-AMH membrane", Desalination 216 (2007), Elsevier, (Oct. 1, 2007),345-355.

Prado Rubio, et al., "Modeling Reverse Electro-Enhanced Dialysis for Integration with Lactic Acid Fermentation", CAPEC, Department of Chemical and Biochemical Engineering Technical University of Denmark (DTU), DK-2800 Lyngby, Denmark, 2009, Available as "A-DK-Prado Rubio-OA-1" at Docstoc.com, http://www.docstoc.com/search/modeling%20reverse%20electro~enhanced%20dialysis%20for%20integration%20with%20lactic-%20acid%20fermentation?catid=0,(Jan. 1, 2009),1-2.

Yi, et al., "An in situ coupling separation process of electro-electrodialysis with back-extraction", Journal of Membrane Science 255 (2005), Elsevier, (Mar. 21, 2005),57-65.

Wong, Edna "Final Office Action", U.S. Appl. No. 12/840,508, (Nov. 27, 2012),1-25.

Wong, Edna "Final Office Action", U.S. Appl. No. 13/357,463, (Sep. 19, 2012),1-17.

Park, Sang H., "International Search Report", PCT Application No. PCT/US2011/033626 (corresponding to U.S. Appl. No. 13/092,685, (Feb. 8, 2012),1-3.

Park, Sang H., "Written Opinion of the International Searching Authority", PCT Application No. PCT/US2011/033626 (corresponding to U.S. Appl. No. 13/092,685, (Feb. 8, 2012),1-4.

Paul, et al., "Reactions of Sodium Metal with Aromatic Hydrocarbons", J. Am. Chem. Soc., 1956, 78 (1), (Jan. 1956),116-120.

Dzik, et al., "Carboxylates as sources of carbon nucleophiles and electrophiles: comparison of decarboxylative and decarbonylative pathways", Chemical Science 2012 vol. 3 Issue No. 9 (2012), (May 3, 2012),2671-78.

Mendez, Zulmariam "Final Office Action", U.S. Appl. No. 12/840,401, (Mar. 15, 2013),1-12.

Wong, Edna "Non Final Office Action", U.S. Appl. No. 13/357,463, (Apr. 9, 2013),1-21.

* cited by examiner

METHOD OF PRODUCING COUPLED RADICAL PRODUCTS FROM BIOMASS

CROSS-REFERENCED RELATED APPLICATIONS

This application claims the benefit of U.S. Provisional Patent Application No. 61/228,078, filed on Jul. 23, 2009. This application also claims the benefit of U.S. Provisional Patent Application No. 61/258,557, filed on Nov. 5, 2009. This application also claims the benefit of U.S. Provisional Patent Application No. 61/260,961, filed on Nov. 13, 2009. This application is a continuation application of U.S. patent application Ser. No. 12/840,508 filed on Jul. 21, 2010, now U.S. Pat. No. 8,506,789, which is a continuation application of U.S. patent application Ser. No. 12/840,401 filed on Jul. 21, 2010. These provisional and non-provisional patent applications are expressly incorporated herein by reference.

BACKGROUND OF THE INVENTION

Hydrocarbon fuels are currently used throughout the world. One specific example of a hydrocarbon fuel is gasoline (which includes octane). Another common hydrocarbon fuel is diesel fuel, which is used in diesel engines. Waxes, oils, and fuels are also desirable hydrocarbon products. Hydrocarbons are used in cosmetic and medical applications.

Biomass is a renewable feedstock. Biomass may comprise lipids (such as fats or oils) that are available from plant, algal, or animal origin. These fats or oils may include fatty acids. Obviously, given its abundance in nature, it is desirable to find a way to use this biomass as a starting material to form a useable product, such as a hydrocarbon fuel.

Current methods to convert biomass to a hydrocarbon fuel involve the process known as "hydroreacting" in which hydrogen gas is added to the biomass (in the presence of a catalyst) to convert the biomass to hydrocarbons. Unfortunately, hydroreacting is generally expensive because hydrogen gas is an expensive reactant. Also, a catalyst is involved in this process, and such catalysts are often intolerant with Ca, Cl, V, N, As, Hg, Si, P, Cr or other materials that may be found in the biomass. Other impurities include soluble vitamins, steroids, terpenes, alkaloids, etc. Another process to convert biomass to hydrocarbons is decarboxylation, wherein the carboxylic acid functionality of a fatty acid is "decarboxylated," thereby leaving a hydrocarbon. (In some situations, this decarboxylation step may be preceded by a fermentation step and/or a hydrolysis step, depending upon the starting material.) Employing the decarboxylation process to produce the hydrocarbon is generally expensive.

Accordingly, there is a need for a new process by which biomass (such as carboxylic acids, oils, etc.) may be converted into a hydrocarbon. It would be desirable for this process to be inexpensive to use and capable of producing a variety of different hydrocarbons. Such a process is disclosed herein.

SUMMARY OF THE INVENTION

Biomass may be obtained from plant, animal, or algal materials and may be comprised of a carbohydrates, lipids, lignins and the like. Biomass may be converted into carboxylic acid, which may be a fatty acid material (or other lipid material). Nonlimiting examples of carboxylic acids may include high-carbon carboxylic acids such as fatty acids (a Carbon content of $C_{12}$ or higher) or low-carbon carboxylic acids (a Carbon content of $C_{12}$ or lower). The carboxylic acids may be aliphatic carboxylic acids or aromatic carboxylic acids. The carboxylic acids may be monocarboxylic acids, dicarboxylic acids, or polycarboxylic acids, depending upon the number of COOH groups contained therein. As used herein throughout, the use of "carboxylic acids" may mean any of the foregoing examples. Similarly, the use of any one of the foregoing examples may be substituted if appropriate for any one of the other foregoing examples. Other embodiments may be designed in which the biomass is obtained through one or more processing steps, before being converted into a carboxylic acid. Such steps may include isolating lipid materials or a carbohydrate material, or lignin material. Obtaining the biomass may also include extracting or converting biomass into lipid materials or a carbohydrate material, or lignin material. It will be appreciated by those of skill in the art that the biomass may already be in the form of a lipid, a carbohydrate, or lignin, fatty acids, or other forms and may need to be extracted, converted, isolated, and the like from the biomass. Thus, the word "obtaining" as used herein throughout may or may not include the steps of extracting, converting, isolating, and the like. Examples of a lipid material include fatty acids, esters of fatty acids, triglycerides of fatty acids, fatty acid derivatives, and/or metal salts of fatty acids. Examples of lignin material may include resins. Examples of carbohydrate material may include cellulose, glucose, among many other examples.

Once this biomass material is obtained (from any source), this material is converted to at least one alkali metal salt of a carboxylic acid. (Typically, this alkali metal salt is a sodium salt, however, other alkali metal salts may also be used.) In some embodiments, conversion of the biomass or biomass material (collectively "biomass") into the alkali metal salt of carboxylic acid involves an intermediate step of conversion into the carboxylic acid itself. Then, depending upon the source of biomass, another conversion reaction may be needed to convert the biomass into an alkali metal salt of carboxylic acid. The terms "alkali salt" and "alkali metal salt" are used interchangeably throughout. For example, if the biomass is a lipid, the lipid may first be hydrolyzed into a carboxylic acid, which in this case may be a fatty acid, and then a "saponification" reaction using a base (such as sodium methoxide or NaOH) is reacted with the carboxylic acid to form the alkali metal salt of carboxylic acid. Examples of saponification reactions are shown below:

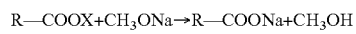

R—COOX+CH₃ONa→R—COONa+CH₃OH

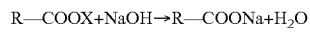

R—COOX+NaOH→R—COONa+H₂O

In the above reactions, "X" is the remaining section of an ester, the remaining section of a triglyceride, hydrogen, or a metal other than an alkali metal. The "R" represents the (carboxylic acid) chain of the lipid material. In embodiments where the biomass is a carbohydrate or a lignin, or some other type of biomass, one or more different intermediate steps may be needed to convert the biomass into an alkali metal salt of carboxylic acid. For example, it may be that the biomass is fermented into the alkali metal salt of carboxylic acid. In other embodiments, the biomass may be fermented into the carboxylic acid and then saponified as described above to from the alkali metal salt of carboxylic acid. It will be appreciated by those of skill in the art that after the conversion steps, if the starting biomass was a lipid, the resulting alkali metal salt of a carboxylic acid may be in the form of an alkali metal salt of a fatty acid. Similarly, where the starting biomass is a carbohydrate, the resulting alkali metal salt of a carboxylic acid may be in the form of an alkali metal salt of a lower carbon carboxylic acid. Likewise, where the starting biomass is a lignin, the resulting alkali metal salt of a carboxylic acid may be in the form of an aromatic carboxylic acid alkali metal salt.

In some embodiments, one more of the intermediate steps are omitted and the biomass is converted directly into at least one alkali metal salt of a carboxylic acid by reacting a base with a quantity of the biomass itself to produce the at least one alkali metal salt of the carboxylic acid. There are many ways to convert biomass into a alkali metal salt of a carboxylic acid.

Continuing with the example where the biomass is a lipid and the intermediate conversion step of saponification has been used (see paragraph 7 above), the next step is to separate the R—COONa and incorporate this chemical into an anolyte for use in an electrolytic cell. This anolyte may also include a solvent (such as methanol) and optionally a supporting electrolyte (in addition to the R—COONa) such as sodium acetate.

The anolyte is fed into an electrolytic cell that uses a sodium ion conductive ceramic membrane that divides the cell into two compartments: an anolyte compartment and a catholyte compartment. A typical membrane is a NaSICON membrane. NaSICON typically has a relatively high ionic conductivity for sodium ions at room temperature. Alternatively, if the alkali metal is lithium, then a particularly well suited material that may be used to construct an embodiment of the membrane is LiSICON. Alternatively, if the alkali metal is potassium, then a particularly well suited material that may be used to construct an embodiment of the membrane is KSICON. Other examples of such solid electrolyte membranes include those based on NaSICON structure, sodium conducting glasses, beta alumina and solid polymeric sodium ion conductors. Such materials are commercially available. Moreover, such membranes are tolerant of impurities that may be in the anolyte and will not allow the impurities to mix with the catholyte. Thus, the impurities (which were derived from the biomass) do not necessarily have to be removed prior to placing the anolyte in the cell.

The electrolytic cell may use standard parallel plate electrodes, where flat plate electrodes and/or flat membranes are used. In other embodiments, the electrolytic cell may be a tubular type cell, where tubular electrodes and/or tubular membranes are used.

An electrochemically active first anode may be found in the cell and may be housed in the first anolyte compartment. The anode may be made of smooth platinum, stainless steel, or may be a carbon based electrode. Examples of carbon based electrodes include boron doped diamond, glassy carbon, synthetic carbon, Dimensionally Stable Anodes (DSA), and lead dioxide. Other materials may also be used for the electrode. The first anode allows the desired reaction to take place. In this anolyte compartment of the cell, the oxidation (decarboxylation) reaction and subsequent radical-radical coupling takes place. In one embodiment, the anodic decarboxylation/oxidative coupling of carboxylic acids occurs via a reaction known as the "Kolbe reaction." The standard Kolbe reaction is a free radical reaction and is shown below:

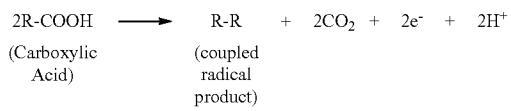
(Carboxylic Acid) (coupled radical product)

This Kolbe reaction is typically conducted in non-aqueous methanolic solutions, with partially neutralized acid (in the form of alkali salt) used with a parallel plate type electrochemical cell. The anolyte used in the cell may have a high density.

As can be seen from the Kolbe reaction, the "R" groups of two carboxylic acid molecules are coupled together, thereby resulting in a coupled radical product. In one embodiment, the Kolbe reaction is a free radical reaction in which two "R radicals" (R.) are formed and are subsequently combined together to form a carbon-carbon bond. It will be appreciated by those of skill in the art, that depending upon the starting material used, the coupled radical product may be a hydrocarbon or some other carboxylic acid chain. The coupled radical product may be a dimer, or a mixed product comprising one or more high- or low-carboxylic acids. The radical in the coupled radical product may include an alkyl-based radical, a hydrogen-based radical, an oxygen-based radical, a nitrogen-based radical, other hydrocarbon radicals, and combinations thereof. Thus, although hydrocarbons may be used in the examples below as the coupled radical product, hydrocarbon may be freely substituted for some other appropriate coupled radical product.

As noted above, however, the present embodiments may use a sodium salt (or alkali metal salt) of the carboxylic acid in the anolyte rather than the carboxylic acid itself. Thus, rather than using the standard Kolbe reaction (which uses a carboxylic acid in the form of a fatty acid), the present embodiments may involve conducting the following reaction at the anode:

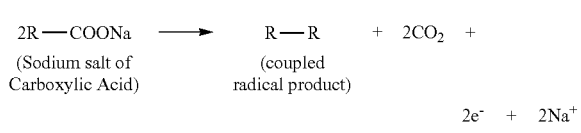
(Sodium salt of Carboxylic Acid) (coupled radical product)

Again, this embodiment results in two "R" groups being coupled together to form a coupled radical product such as a hydrocarbon. There are distinct advantages of using the sodium salt of the carboxylic acid instead of the carboxylic acid itself:

R—COONa is more polar than R—COOH and so it is more likely to decarboxylate (react) at lower voltages;

The electrolyte conductivity may be higher for sodium salts of carboxylic acids than carboxylic acids themselves; and The anolyte and catholyte may be completely different allowing different reactions to take place at either electrode.

As noted above, the cell contains a membrane that comprises a sodium ion conductive membrane. This membrane selectively transfers sodium ions (Na$^+$) from the anolyte compartment to the first catholyte compartment under the influence of an electrical potential, while at the same time preventing the anolyte and catholyte from mixing.

The catholyte may be aqueous NaOH or a non aqueous methanol/sodium methoxide solution. (The anolyte may also be aqueous or non-aqueous). An electrochemically active cathode is housed in the catholyte compartment, where reduction reactions take place. These reduction reactions may be written as:

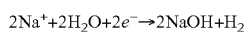

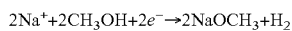

Hydrogen gas is the product of the reduction reaction at the cathode. NaOH (sodium hydroxide) or NaOCH$_3$ (sodium methoxide) is also produced. This NaOH or NaOCH$_3$ is the base that was used above in the saponification reaction. Thus, this reaction may actually regenerate (in the catholyte compartment) one of the reactants needed in the overall process. This NaOH or NaOCH$_3$ may be recovered and re-used in further reactions. The ability to regenerate and re-use the NaOH or NaOCH$_3$ is advantageous and may significantly reduce the overall costs of the process.

In an alternative embodiment, a sodium salt of carboxylic acid with a small number of carbon atoms (such as CH$_3$COONa (sodium acetate)) may be added to the anolyte in addition to the R—COONa. The addition of sodium acetate may be advantageous in some embodiments because:

Sodium acetate may act as a suitable supporting electrolyte as it is highly soluble in methanol solvent (up to 26 wt. %), thereby providing high electrolyte conductivity in the anolyte;

Sodium acetate will itself decarboxylate (in the electrolytic process) and produce CH$_3$. (methyl radicals) by the following reaction:

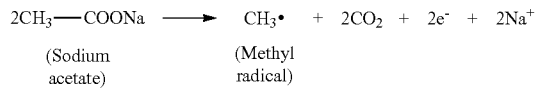

(Sodium acetate) (Methyl radical)

In turn, the methyl radical may react with a hydrocarbon group of the carboxylic acid to form hydrocarbons with additional CH$_3$— functional group:

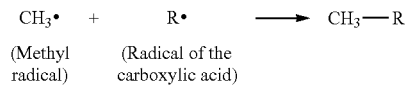

(Methyl radical) (Radical of the carboxylic acid)

Therefore, in one embodiment, by using sodium acetate as part of the anolyte, this embodiment may couple two hydrocarbon radicals from the carboxylic acid together (R—R) or couple the radical of the carboxylic acid with a methyl radical from the acetate (R—CH$_3$), thereby producing mixed hydrocarbon products. This mixture of products may be separated and used as desired. Of course, this embodiment is shown using sodium acetate as the additional reactant. In the alternative, other sodium salts of a carboxylic acid with a small number of carbon atoms may also be used to couple a carbon radical to the radical of the carboxylic acid.

It will be appreciated that a variety of different hydrocarbons or coupled radical products may be formed using the present embodiments. For example, the particular "R" group that is selected may be chosen and/or tailored to produce a hydrocarbon that may be used for diesel, gasoline, waxes, JP8 ("jet propellant 8"), etc. The particular application of the hydrocarbon may depend upon the starting material chosen.

BRIEF DESCRIPTION OF THE SEVERAL VIEWS OF THE DRAWINGS

In order that the manner in which the above-recited and other features and advantages of the invention are obtained will be readily understood, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which.

DETAILED DESCRIPTION

Figure 1:
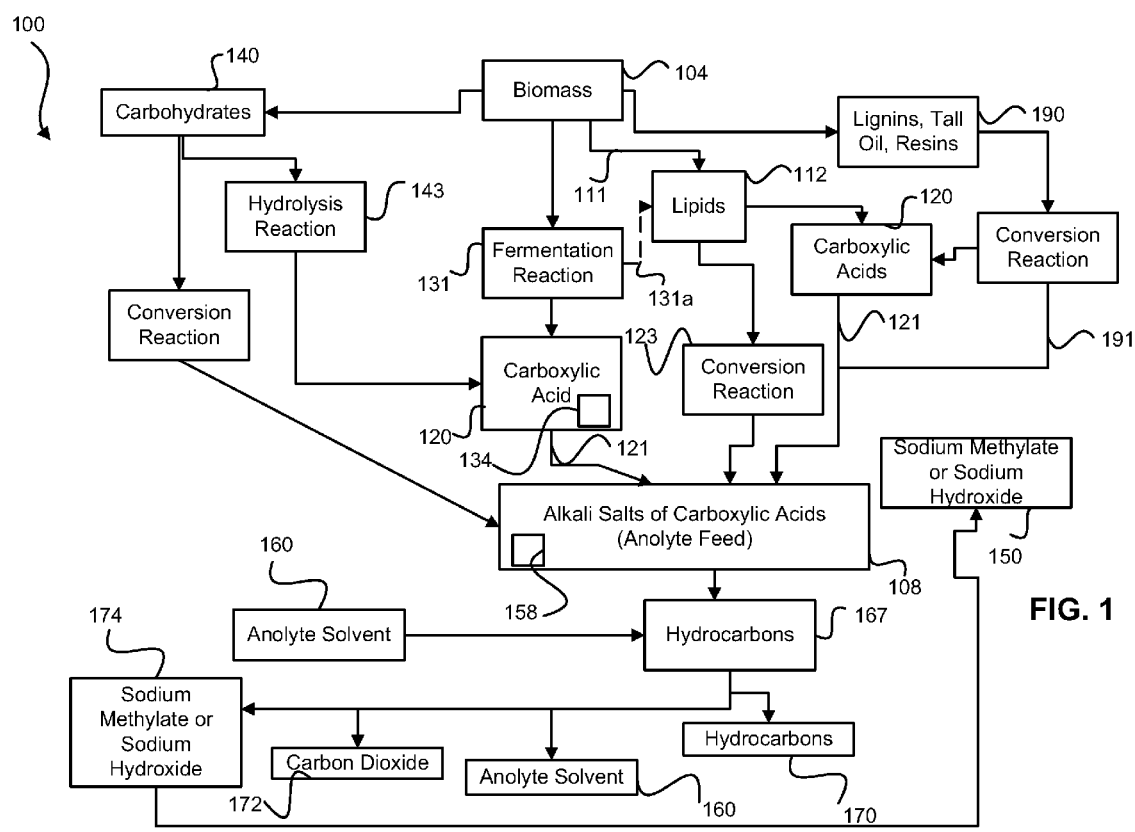
FIG. 1 is a schematic diagram illustrating various embodiments of processes that may be used to produce a coupled radical product in the form of hydrocarbon from biomass.

A method for producing a coupled radical product from biomass is disclosed. This method comprises obtaining a quantity of biomass and then converting the biomass into an at least one alkali metal salt of a carboxylic acid. In some embodiments, the alkali metal may comprise sodium such that the alkali metal salt of the carboxylic acid comprises a sodium salt of the carboxylic acid. An anolyte may comprise a quantity of the alkali metal salt of the carboxylic acid. In one embodiment, the alkali metal salt of the carboxylic acid is decarboxylated. The decarboxylation converts the alkali metal salt of the carboxylic acid into an alkyl radical that reacts to form the coupled radical product. In one embodiment, the coupled radical product is a hydrocarbon. A mixture of hydrocarbons may also be produced. The alkyl radical may couple to another alkyl radical or to a hydrogen radical. The hydrogen radicals may be formed in addition to the alkyl radicals. The hydrogen radicals may also be formed from an alkali metal formate or from a photolysis process of hydrogen gas within the anolyte compartment. It will be appreciated by those of skill in the art that any irradiation process may be used instead of photolysis. The decarboxylation of the alkali metal salt of the carboxylic acid may also be performed via photolysis. At least one alkali metal salt of the carboxylic acid may further comprise a quantity of an alkali metal acetate and/or a quantity of an alkali metal formate.

The biomass may be converted into at least one alkali metal salt of a carboxylic acid in a variety of different ways. For example, embodiments may be constructed in which converting the biomass comprises saponification, wherein a base is reacted with a quantity of the carboxylic acid to produce the alkali metal salt of the carboxylic acid. In other embodiments, a lipid is extracted from the biomass, and, if necessary, the lipid may be hydrolyzed to form carboxylic acid. This carboxylic acid may then be saponified to produce at least one alkali metal salt of carboxylic acid. In other embodiments, the biomass is fermented to produce a carboxylic acid. The carboxylic acid may then be saponified to produce at least one alkali metal salt of carboxylic acid. In other embodiments, the biomass is fermented to directly produce at least one alkali metal salt of carboxylic acid. Further embodiments are designed in which a carbohydrate is hydrolyzed to produce a carboxylic acid (which may then be saponified). The saponification may occur in the same electrolytic cell where decarboxylation occurs. In other embodiments, a base is reacted directly with a quantity of biomass to produce the at least one alkali metal salt of the carboxylic acid. Accordingly, the alkali metal salt may be derived from carbohydrates, lipids, such as oils, including tall oil, fatty acids, esters of fatty acids, triglycerides of fatty acids, phospholipids, fatty acid derivatives, and/or metal salts of fatty acids, lignins, such as resins, and mixtures of the foregoing. The alkali metal salt of the carboxylic acid may be derived from the forgoing in the form of wood chips, forestry residue, energy crops (switch grass, miscanthus, sorghum, energy cane and other genetically modified plants), algae, cyanobacteria, jatropha, soy bean, corn, palm, coconut, canola, rapeseed, Chinese tallow, animal fats and products of genetically modified organisms, whether natural, synthetic, man-made, or even genetically altered.

The electrolytic cell used to decarboxylate alkali metal salt of the carboxylic acid may comprise an anolyte compartment and a catholyte compartment. The anolyte compartment houses the anolyte and the catholyte compartment houses a catholyte. The anolyte compartment and the catholyte compartment are separated by an alkali ion conducting membrane. In some embodiments, the alkali ion conducting membrane is a NaSICON membrane. During this reaction, the catholyte in the catholyte compartment produces hydrogen gas and a base. This base may or may not be the same base used in the saponification reaction that produces the alkali metal salt of the carboxylic acid. The anolyte and catholyte may both comprise a solvent. The anolyte may comprise a first solvent or a first mixture of solvents, and the catholyte may comprise a second solvent or second mixture of solvents, wherein the first solvent or the first mixture of solvents included in the anolyte do not have to be the same as the second solvent or the second mixture of solvents included in the catholyte. The first solvent may comprise a two-phase solvent system, wherein one phase is capable of dissolving ionic materials and the other phase is capable of dissolving non-ionic materials. The anolyte may be reacted at a higher temperature and/or pressure than the catholyte (or vice versa).

A method for producing a coupled radical product is also disclosed. The method comprises preparing an anolyte for use in an electrolytic cell, the cell comprising an alkali ion conducting membrane, wherein the anolyte comprises a first solvent and a quantity of an alkali metal salt of a carboxylic acid. The method also comprises decarboxylating at least one alkali metal salt of the carboxylic acid within the cell, wherein the decarboxylation converts at least one alkali metal salt of the carboxylic acid into an alkyl radical that reacts to form a coupled radical product. In one embodiment, the coupled radical product is a hydrocarbon.

Another method of producing a coupled radical product is also disclosed. The method may comprise obtaining a alkali metal salt of a carboxylic acid, the alkali metal salt being derived from, for example, carbohydrates, fatty acids, dicarboxylic fatty acids, polycarboxylic fatty acids, esters of fatty acids, triglycerides of fatty acids, lipids, phospholipids, fatty acid derivatives, and/or metal salts of carboxylic acids. The method may also comprise preparing an anolyte for use in an electrolytic cell, the electrolytic cell comprising an anolyte compartment, a catholyte compartment, and a NaSICON membrane that separates the anolyte compartment from the catholyte compartment, wherein anolyte is housed within the anolyte compartment and catholyte is housed within the catholyte compartment. The anolyte comprises a solvent and a quantity of the sodium salt of the carboxylic acid. The anolyte is electrolyzed within the cell, wherein the electrolyzing decarboxylates the sodium salt of the carboxylic acid and converts the sodium salt of the carboxylic acid into an alkyl radical that reacts to form a coupled radical product, which in one embodiment, may be a hydrocarbon.

The embodiments of the present invention will be best understood by reference to the drawings, wherein like parts are designated by like numerals throughout. It will be readily understood that the components of the present invention, as generally described and illustrated in the figures herein, could be arranged and designed in a wide variety of different configurations. Thus, the following more detailed description of the present embodiments, as represented in the Figures, is not intended to limit the scope of the invention, as claimed, but is merely representative of embodiments of the invention.

FIG. 1 is a schematic diagram of an embodiment of the method (process) 100 described herein. Specifically, this process involves obtaining a quantity of biomass 104. The biomass 104 may comprise, for example, carbohydrates, lipids, such as oils, including tall oil, and lignins, such as resins. The biomass may also include lipids such as fatty acids, esters of fatty acids, triglycerides of fatty acids, phospholipids, fatty acid derivatives, and/or metal salts of fatty acids. Other examples of biomass include wood chips, forestry residue, energy crops (switch grass, miscanthus, sorghum, energy cane and other genetically modified plants), algae, cyanobacteria, jatropha, soy bean, corn, palm, coconut, canola, rapeseed, Chinese tallow, animal fats and products of genetically modified organisms. The biomass may be a variable or impure feedstock. As indicated above, the biomass 104 may be from algal, animal, microbial, or plant origins (such as wood, switch grass, etc.). In one embodiment, any type of biomass may be used, whether the source of this biomass 104 is natural, synthetic, man-made, or even genetically altered (such as in the case of microbes, microorganisms, or animals). If the biomass is from an algal material, the algae may be synthesized, genetically-altered, or may be naturally occurring. Mixtures of different types of biomass may also be used. As explained in detail herein, the biomass 104 may be used as a starting material to ultimately arrive at an alkali metal salt of a carboxylic acid 108 (which may be referred to as an "alkali metal salt of a fatty acid" 108 as used in the description below).

As shown in FIG. 1, there are a variety of different methods, processes, and/or chemical reactions that will convert the biomass 104 into the alkali salt of the fatty acid. In some embodiments, the produced alkali metal salt of the carboxylic acid comprises a sodium salt. Other alkali metal salts, such as lithium salts or potassium salts, may also be used. For example, in one embodiment, the biomass 104 will be converted via an extraction process 111 into a lipid material 112. This lipid material 112 may be a synthetic or naturally occurring lipid, microbially produced (either biochemically or chemically), branched or unbranched, saturated or unsaturated, or any other type of lipid material. Examples of this lipid material 112 include phospholipids, steroids, oils, waxes, fatty acids, esters of fatty acids, triglycerides of fatty acids, fatty acid derivatives, and/or metal salts of fatty acids. Dicarboxylic acids, tricarboxylic acids, olego carboxylic acids, or polycarboxylic acids may also be used as the lipid.

This lipid material 112 may be subjected to a hydrolysis process 115 that converts the lipid 112 into a fatty acid 120

(such as carboxylic acid 120). In turn, this fatty acid 120 may undergo a saponification reaction 121 to produce the alkali salt of the fatty acid 108. As shown in FIG. 1, the saponification reaction may involve reacting the fatty acid 120 with a base 150. Examples of the base 150 include sodium hydroxide, sodium methoxide, sodium methylate, sodium ethoxide or another caustic agent. Other embodiments may be designed in which the reaction is accomplished via another sodium containing compound (or alkali metal containing compound) or even metallic sodium or another metallic alkali metal. Additionally or alternatively, the lipid 112 may be subjected to a conversion reaction 123 (such as an alkali metal hydrolysis and/or a saponification process) which converts the lipid 112 into at least one alkali metal salt of the fatty acid 108.

The saponification reaction uses the base 150 to produce an alkali metal salt of a fatty acid. Examples of this reaction are shown below using sodium methoxide or NaOH as the base:

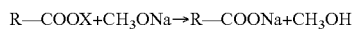

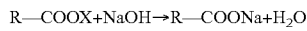

The "R" in this embodiment represents the hydrocarbon tail or hydrocarbon moiety of the molecule. The "X" represents the remaining section of an ester, the remaining section of a triglyceride, a hydrogen or a metal other than sodium. As shown by this reaction, R—COONa is produced, which is the sodium salt of the fatty acid.

As shown in FIG. 1, in other embodiments, the biomass 104 may undergo a fermentation reaction 131 that converts the biomass 104 into a fatty acid 120. In some embodiments, this fatty acid may be acetic acid 134. The acetic acid 134 and/or the fatty acid 120 may then undergo the saponification reaction 121 to produce the alkali salt of the fatty acid 108. If acetic acid 134 is obtained, the saponification reaction will produce a quantity of an alkali acetate 158. Optionally, the alkali salt of the fatty acid 108 may be mixed with an alkali acetate 158. The acetate 158 may be obtained from any suitable source, including the biomass itself. Other types of conversion reactions 123 may also be used. Other embodiments may be designed in which algae, or algae products, are converted directly to an alkali metal salt of the fatty acid.

In other embodiments, the fermentation reaction 131 may convert the biomass 104 into a lipid material 112, as shown by dashed line 131a. This is especially useful for biomass from tall oils, pulp produced from paper mills, etc. Such lipid materials 112 may then be processed in the manner outlined above.

In other embodiments, the biomass 104 may be a carbohydrate 140. This carbohydrate material 140 may undergo a hydrolysis reaction 143 that converts the carbohydrate into acetic acid 134 and/or into another fatty acid 120. The particular carbohydrate material used will determine whether the resulting acid is branched or unbranched, saturated or unsaturated. Examples of carbohydrates could be starch, cellulose, hemi-cellulose, glucose, pentoses, and sucrose. Once the acetic acid 134 or fatty acid 120 has been obtained, this acid may be subjected to saponification 121 to produce the alkali salt of the fatty acid 108. Other types of conversion reactions that convert the carbohydrate into the alkali salt of the fatty acid 108 may also be used.

In other embodiments, the biomass 104 comprises tall oil, resins, and/or lignins 190. Such materials may be converted 192 into carboxylic acids 120 (and then processed as outlined herein). In one embodiment, the lignin 190 is first subjected to a conversion reaction 192 whereby the lignin is hydrolyzed into carboxylic acid and then saponified into the alkali metal salt of carboxylic acid. In other embodiments, the materials 190 may be directly converted 191 to the alkali metal salts of carboxylic acids.

It should be noted that the various processes described and shown in FIG. 1 are not limiting. In certain embodiments, any type of biomass may be used. Also, other processes may be employed within the disclosed methods.

Figure 2:
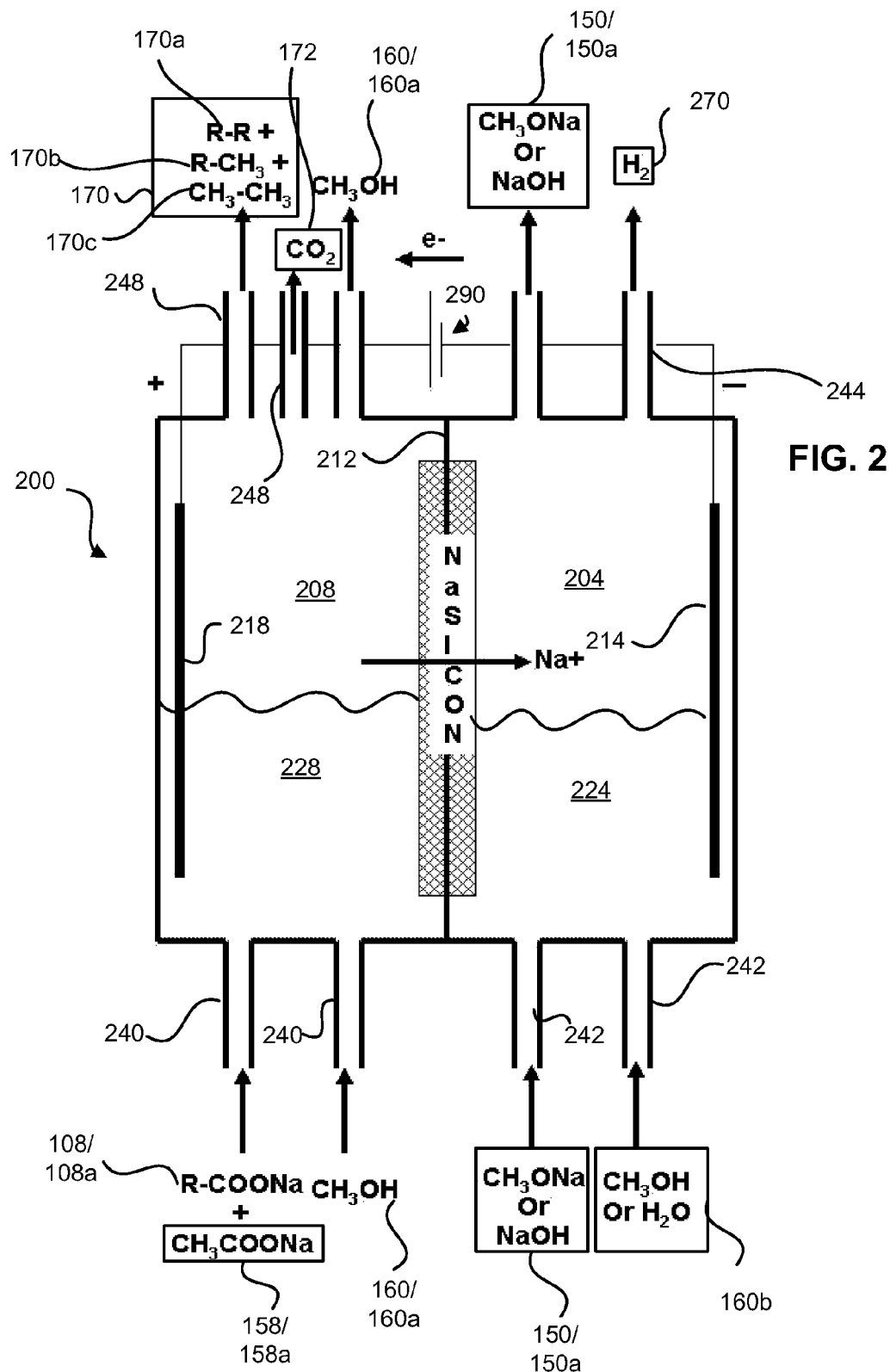
FIG. 2 is a schematic view of an electrolytic cell for conversion of sodium salts of fatty acids to coupled radical products by anodic decarboxylation and subsequent carbon-carbon bond formation in accordance with the present embodiments.

Once the alkali salt of the fatty acid 108 has been obtained, the salt of the fatty acid 108 will be added to an electrochemical cell that includes a sodium conducting membrane (or other alkali conducting membrane). An example of a typical embodiment of a cell is shown in FIG. 2. This cell, which may also include a quantity of a first solvent 160 (which may be, for example, an alcohol like methanol, ethanol, and/or glycerol), may use an advanced Kolbe reaction 167. The solvent 160 may be obtained from the base 150, or may be obtained from any other source. This advanced Kolbe reaction produces a hydrocarbon 170 along with a quantity of carbon dioxide 172 and a base 174. As discussed above, in certain embodiments, the hydrocarbon 170 is but one example of any of a number of coupled radical products that may be produced by this process. The base 174 may be the same as the base 150 that was used in the saponification reaction 121. By forming the base as part of the reaction, the base used in saponification may be regenerated and recycled over the entire process. The regeneration of the base 150 obviates the need to purchase new quantities of base in order to repeat the process. Likewise, because the base is re-used, disposal costs associated with disposing of the base may be avoided. Similarly, the carbon dioxide 172 produced in the process 100 is a safe, naturally-occurring chemical and may be disposed of, collected, sold, etc.

The hydrocarbon 170 produced in the process 100 (and more specifically in the advanced Kolbe reaction 167) may be of significant value. Hydrocarbons have significant value for use in fuels, diesel fuels, gasoline, medical applications, waxes, perfumes, oils, and other applications and products. With the process of the present invention, different types of hydrocarbons may be used. Hydrocarbons are often classified by the number of carbons in their chain. In addition, hydrocarbons may often be classified into the following "fractions":

$C_1$ Methane fraction
$C_2$-$C_5$ Natural gas fraction
$C_6$-$C_{10}$ Gasoline fraction
$C_{10}$-$C_{13}$ JP8 fraction
$C_{14}$-$C_{20}$ Diesel fraction
$C_{20}$-$C_{25}$ Fuel Oil fraction
$C_{20}$-$C_{30}$ Waxes Note that these classifications are not exact and may change according to the particular embodiment. For example, the "gasoline fraction" could have a portion of $C_{11}$, the JP8 fraction could have some $C_{14}$, etc.

By forming the coupled radical products according to the present embodiments, various hydrocarbons could be made in some or all of these fractions. For example, embodiments may be constructed in which a $C_8$ hydrocarbon (octane) is formed, which is a principal ingredient in commercial gasoline Likewise, a $C_{12}$ hydrocarbon may be formed, which may be used in making JP8. Of course, the exact product that is obtained depends upon the particular starting material(s) and/or the reaction conditions used. Thus, the present embodiments allow biomass to be converted into synthetic lubricants, gasoline, JP8, diesel fuels, or other hydrocarbons.

In order to form the hydrocarbon, an advanced Kolbe reaction 167 occurs within an electrochemical cell. This reaction, along with an example of a typical cell, will now be described in greater detail in conjunction with FIG. 2. Specifically, FIG. 2 shows a cell 200 (which may be an electrochemical cell to which a voltage may be applied). The cell 200 includes a catholyte compartment 204 and an anolyte compartment 208. The catholyte compartment 204 and the anolyte compartment 208 may be separated by a membrane 212.

The particulars of each cell 200 will depend upon the specific embodiment. For example, the cell 200 may be a standard parallel plate cell, where flat plate electrodes and/or flat plate membranes are used. In other embodiments, the cell 200 may be a tubular type cell, where tubular electrodes and/or tubular membranes are used. An electrochemically active first anode 218 is housed, at least partially or wholly, within the anolyte compartment 208. More than one anode 218 may also be used. The anode 218 may comprise, for example, a smooth platinum electrode, a stainless steel electrode, or a carbon based electrode. Examples of a typical carbon based electrode include boron doped diamond, glassy carbon, synthetic carbon, Dimensionally Stable Anodes (DSA) and relatives, and/or lead dioxide. Other electrodes may comprise metals and/or alloys of metals, including S.S, Kovar, Inconel/monel. Other electrodes may comprise $RuO_2$—$TiO_2$/Ti, $PtO_x$—$PtO_2$/Ti, $IrO_x$, $Co_3O_4$, $MnO_2$, $Ta_2O_5$ and other valve metal oxides. In addition, other materials may be used to construct the electrode such as $SnO_2$, $Bi_2Ru_2O_7$ (BRO), $BiSn_2O_7$, noble metals such as platinum, titanium, palladium, and platinum clad titanium, carbon materials such as glassy carbon, BDD, or Hard carbons. Additional embodiments may have $RuO_2$—$TiO_2$, hard vitrems carbon, and/or $PbO_2$. Again, the foregoing serve only as examples of the type of electrodes that may be employed. The cathode compartment 204 includes at least one cathode 214. The cathode 214 is partially or wholly housed within the cathode compartment 204. The material used to construct the cathode 214 may be the same as the material used to construct the anode 218. Other embodiments may be designed in which a different material is used to construct the anode 218 and the cathode 214.

The anolyte compartment 208 is designed to house a quantity of anolyte 228. The catholyte compartment 204 is designed to house a quantity of catholyte 224. In the embodiment of FIG. 2, the anolyte 228 and the catholyte 224 are both liquids, although solid particles and/or gaseous particles may also be included in either the anolyte 228, the catholyte 224, and/or both the anolyte 228 and the catholyte 224.

The anode compartment 208 and the cathode compartment 204 are separated by an alkali metal ion conductive membrane 212. The membrane utilizes a selective alkali metal transport membrane. For example, in the case of sodium, the membrane is a sodium ion conductive membrane 212. The sodium ion conductive solid electrolyte membrane 212 selectively transfers sodium ions ($Na^+$) from the anolyte compartment 208 to the catholyte compartment 204 under the influence of an electrical potential, while preventing the anolyte 228 and the catholyte 224 from mixing. Examples of such solid electrolyte membranes include those based on NaSICON structure, sodium conducting glasses, beta alumina and solid polymeric sodium ion conductors. NaSICON typically has a relatively high ionic conductivity at room temperature. Alternatively, if the alkali metal is lithium, then a particularly well suited material that may be used to construct an embodiment of the membrane is LiSICON. Alternatively, if the alkali metal is potassium, then a particularly well suited material that may be used to construct an embodiment of the membrane is KSICON.

As noted above, the saponification reaction 121 and/or the other reactions of FIG. 1 are designed to produce a quantity of an alkali metal salt of a fatty acid 108. This alkali metal salt of a fatty acid 108 may be separated and/or purified, as needed. Likewise, as desired, if the alkali metal salt of a fatty acid 108 comprises a mixture of fatty acid salts, these compounds may be separated. Alternatively, the alkali metal salt of a fatty acid 108 may not be separated and may comprise a mixture of different fatty acid salts. As explained above, the alkali metal salt of a fatty acid 108 may have a structure R—COO—AlMet, wherein "R" represents the fatty acid moiety, and "AlMet" represents the alkali metal ion. For example, if the alkali metal is sodium, then the alkali metal salt of a fatty acid 108 will generally have the structure R—COONa.

The anolyte compartment 208 may include one or more inlets 240 through which the anolyte 228 may be added. Alternatively, the components that make up the anolyte 228 may be separately added to the anolyte compartment 208 via the inlets 240 and allowed to mix in the cell. The anolyte includes a quantity of the alkali metal salt of a fatty acid 108. In the specific embodiment shown in FIG. 2, sodium is the alkali metal, so that alkali metal fatty acid salt 108 is a sodium salt 108a. The anolyte 228 also includes a first solvent 160, which as noted above, may be an alcohol 160a. Of course, other types of solvents may also be used. The anolyte 228 may optionally include the alkali metal acetate 158, such as sodium acetate 158a.

The catholyte compartment 204 may include one or more inlets 242 through which the catholyte 224 may be added. The catholyte 224 includes a second solvent 160b. The second solvent 160b may be an alcohol or water (or a mixture of alcohol and water). Significantly, the solvent 160b in the catholyte 224 is not necessarily the same as the first solvent 160a in the anolyte 228. In some embodiments, the solvents 160a, 160b may be the same. The reason for this is that the membrane 212 isolates the compartments 208, 204 from each other. Thus, the solvents 160a, 160b may be each separately selected for the reactions in each particular compartment (and/or to adjust the solubility of the chemicals in each particular compartment). Thus, the designer of the cell 200 may tailor the solvents 160a, 160b for the reaction occurring in the specific compartment, without having to worry about the solvents mixing and/or the reactions occurring in the other compartment. This may be a significant advantage in designing the cell 200. A typical Kolbe reaction only allows for one solvent used in both the anolyte and the catholyte. Accordingly, the use of two separate solvents may be advantageous. In other embodiments, either the first solvent 160a, the second solvent 160b, and/or the first and second solvents 160a, 160b may comprise a mixture of solvents.

The catholyte 224 may also include a base 150. In the embodiment of FIG. 1, the base 150 may be NaOH or sodium methoxide, or a mixture of these chemicals. The base 150 may be the same base 150 as used in the saponification reaction 121 of FIG. 1. Alternatively, the base may be a different base than that which was used in the saponification reaction (as shown by reference number 150a).

The reactions that occur at the anode 218 and cathode 214 will now be described. As with all electrochemical cells, such reactions may occur when voltage source 290 applies a voltage to the cell 200.

At the cathode 214, a reduction reaction takes place. This reaction uses the sodium ions and the solvent to form hydrogen gas 270 as well as an additional quantity of base 150/150a. Using the chemicals of FIG. 2 as an example, the reduction reaction may be written as follows:

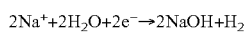

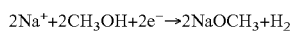

The hydrogen gas 270 and/or the base 150/150a may be extracted through outlets 244. The hydrogen gas 270 may be gathered for further processing for use in other reactions, and/or disposed of or sold. The production of the base 150/150a may be a significant advantage because the base 150 that was consumed in the saponification reaction 121 of FIG. 1 is generated in this portion of the cell 200. Thus, the base formed in the cell may be collected and re-used in future saponification reactions (or other chemical processes). As the base may be re-used, the hassle and/or the fees associated with disposing of the base are avoided.

The reactions that occur at the anode 218 may involve decarboxylation. These reactions may involve an advanced Kolbe reaction (which is a free radical reaction) to form a quantity of a hydrocarbon 170 and carbon dioxide 172. Using the chemicals of FIG. 2 as an example, the oxidation reactions may be written as follows:

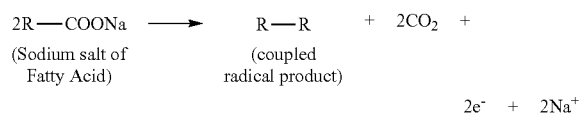

The carbon dioxide 172 may be vented off (via outlets 248). This is a safe, naturally-occurring chemical that may be collected, disposed of, or re-used. The coupled radical product 170 may also be collected via an outlet 248. For example, a quantity of the solvent 160/160a may be extracted via an outlet 248 and recycled, if desired, back to the inlet 240 for future use.

The advanced Kolbe reaction may comprise a free radical reaction. As such, the reaction produces (as an intermediate) a hydrocarbon radical designated as R. Accordingly, when two of these R. radicals are formed, these radicals may react together to form a carbon-carbon bond:

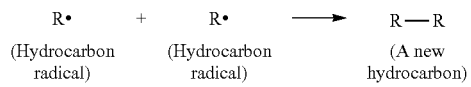

As shown in FIG. 2, this R—R hydrocarbon product is designated as hydrocarbon 170a. In essence, the R moiety is being decarboxylated, as the carbonyl moiety is removed, leaving only the R. radical that is capable of reacting to form a hydrocarbon.

As shown in FIG. 2, sodium acetate 158a (or some other sodium salt of carboxylic acid with a small number of carbon atoms) may be part of (or added to) the anolyte 228. Sodium acetate may act as a suitable supporting electrolyte as it is highly soluble in methanol solvent (up to 26 wt. %) providing high electrolyte conductivity. At the same time, sodium acetate may itself decarboxylate as part of the advanced Kolbe reaction and produce $CH_3\cdot$ (methyl) radicals by the following reaction:

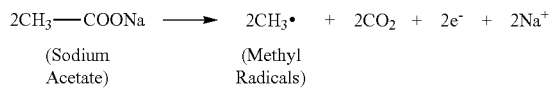

The methyl radicals may then be reacted with hydrocarbon group of the fatty acid to form hydrocarbons with additional $CH_3$— functional group:

$$CH_3\cdot + R\cdot \rightarrow CH_3—R$$

Alternatively or additionally, the methyl radical may react with another methyl radical to form ethane:

$$CH_3\cdot + CH_3\cdot \rightarrow CH_3—CH_3$$

Ethane ($CH_3$—$CH_3$) is a hydrocarbon that may form a portion of the hydrocarbon product 170. This ethane is designated as 170c. The $CH_3$—R formed in the reaction may also be part of the hydrocarbon product 170 and is designated as 170b. Thus, a mixture of hydrocarbons may be obtained. If desired, the various hydrocarbons 170a, 170b, 170c may be separated from each other and/or purified, such as via gas chromatography or other known methods. The present embodiments may couple two hydrocarbon radicals or couple methyl radicals with hydrocarbon radicals. The amount of the $CH_3$—R or R—R in the product may depend upon the particular reaction conditions, quantities of reactants used in the anolyte, etc.

The foregoing example involved the use of sodium acetate in addition to the fatty acid salt to produce reactive methyl radicals, thereby producing $CH_3$—R in addition to the R—R product. However, rather than acetate, other salts that have a small number of carbons may be used in place of or in addition to acetate. These salts having a small number of carbons may produce, for example, ethyl radicals, propyl radicals, isopropyl radicals, and butyl radicals during decarboxylation. Thus, by changing the optional component, additional hydrocarbons may be formed in the cell 200. The user may thus tailor the specific product formed by using a different reactant. Thus, it is possible to create a mixture of products as different alkyl radicals react together or even react with a methyl radical, a hydrogen radical, etc. The different alkyl radicals may be added by adding acetate, formate, etc. into the anolyte through, for example, an additional port in the anolyte compartment. Such a different mixture of products may be, in some embodiments, similar to what would occur in a disproportionation reaction.

In a similar manner, instead of and/or in addition to using sodium acetate, an alkali metal formate (such as sodium formate) may be used as part of the anolyte. Sodium formate has the formula H—COONa. During the electrochemical reaction, the formate, like the acetate, will undergo decarboxylation to form a hydrogen radical:

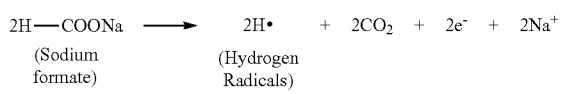

In turn, this hydrogen radical will react to form:

$$H\cdot + R\cdot \rightarrow H—R$$

AND/OR $$H\cdot + H\cdot \rightarrow H_2$$

The use of sodium formate as an optional reactant may result in the R—R product being formed as well as a quantity of an R—H product (and even a quantity of hydrogen gas ($H_2$)). (The hydrogen gas may be re-used if desired). The use of formate may prevent the unnecessary formation of ethane and/or may be used to tailor the specific hydrocarbon (R—H) product.

The particular R group that is shown in these reactions may be any "R" obtained from biomass, whether the R includes saturated, unsaturated, branched, or unbranched chains.

When the R—R product is formed, this is essentially a "dimer" of the R group. For example, if the R group is $CH_3$ (such as is the case with sodium acetate), two methyl radicals react $(2CH_3\cdot)$ and "dimerize" into ethane $(CH_3—CH_3)$. If the R group is a $C_{18}H_{34}$ hydrocarbon, then a $C_{36}H_{78}$ product may be formed. By using these simple principles, as well as using the formate or the small chain carbon salt, any desired hydrocarbon may be obtained. For example, by using a $C_4$ sodium salt, a $C_8$ R—R hydrocarbon may be formed, which may be useable as part of a gasoline. Likewise, if a $C_6$ sodium salt is used, a $C_{12}$ R—R hydrocarbon may be formed, which may be useable as JP8. Synthetic lubricants, waxes, and/or other hydrocarbons may be formed in the same or a similar manner.

Figure 3:
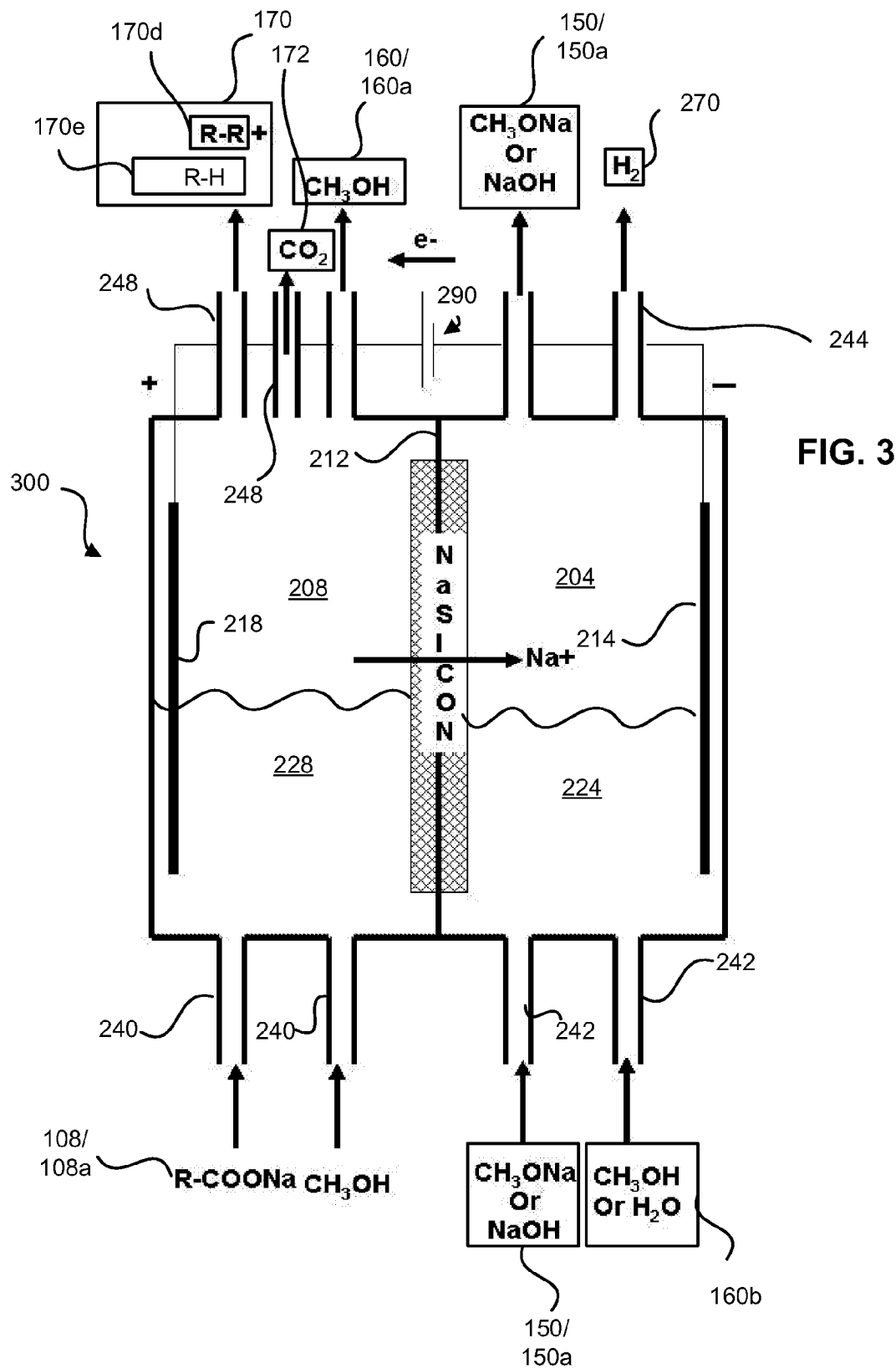
FIG. 3 is a schematic view of another embodiment of an electrolytic cell for conversion of sodium salts of fatty acids to coupled radical products.

An alternate embodiment to that of FIG. 2 will now be described with reference to the embodiment shown in FIG. 3. Because much of the embodiment of FIG. 3 is similar to that which is shown in FIG. 2, a discussion of portions of the similar features will be omitted for purposes of brevity, but is incorporated herein by this reference. Because the anolyte compartment 208 is separate from the catholyte compartment 204, it is possible to create a reaction environment in the anolyte compartment 208 that is different from the catholyte compartment 204. FIG. 3 illustrates this concept. For example, hydrogen gas $(H_2)$ 320 may be introduced into the anolyte compartment 208. In some embodiments, the anolyte compartment 208 may be pressurized by hydrogen gas 320. In some embodiments, the anode 208 or anolyte could include a component 310 made of Pd or other noble metal (such as Rh, Ni, Pt, Ir, or Ru) or another substrate such as Si, a zeolite, etc. (This component may be all or part of the electrode and may be used to immobilize the hydrogen gas on the electrode.) Alternatively, Pd or Carbon with Pd could be suspended within the cell. The effect of having hydrogen gas in the anolyte compartment 208 is that the hydrogen gas may form hydrogen radicals (H.) during the reaction process that react in the manner noted above. These radicals would react with the R. radicals so that the resulting products would be R—H and R—R. If sufficient hydrogen radicals (H.) are present, the R—H product may be predominant, or may be the (nearly) exclusive product. This reaction could be summarized as follows (using Pd as an example of a noble metal, noting that any other noble metal could be used):

R—COONa+$H_2$ and Pd→Pd—$H_x$→Pd+H—R+$CO_2$+$e^-$+$Na^+$

By using one or more of the noble metals with hydrogen gas in the anolyte compartment, the particular product (R—H) may be selected. In the embodiment of FIG. 3, hydrogen gas 270 is produced in the catholyte compartment 204 as part of the reduction reaction. This hydrogen gas 270 may be collected and used as the hydrogen gas 320 that is reacted with the noble metal in the anolyte compartment 208. Thus, the cell 300 actually may produce its own hydrogen gas 270 supply that will be used in the reaction. Alternatively, the hydrogen gas 270 that is collected may be used for further processing of the hydrocarbon, such as cracking and/or isomerizing waxes and/or diesel fuel. Other processing using hydrogen gas may also be used. The R—H product helps to minimize the formation of the R—R group (which, if the R group is sufficiently, large, may be a hydrocarbon such as a wax).

Figure 4:
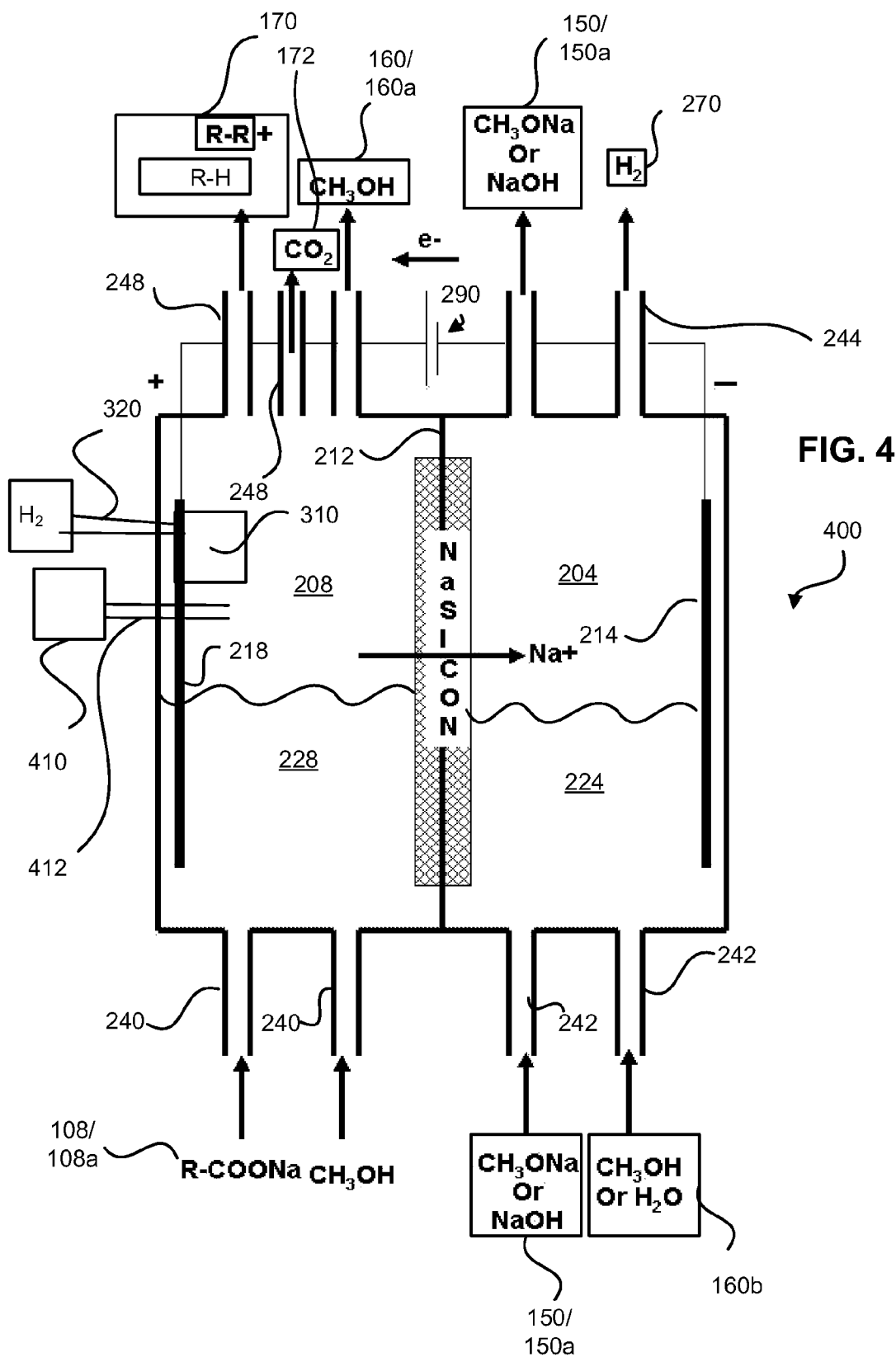
FIG. 4 is a schematic view of another embodiment of an electrolytic cell for conversion of sodium salts of fatty acids to coupled radical products.

Referring now to FIG. 4, an additional embodiment of a cell 400 is illustrated. The cell 400 is similar to the cells that have been previously described. Accordingly, for purposes of brevity, much of this discussion will not be repeated. In the embodiment of FIG. 4, the cell 400 is designed such that one or more photolysis reactions may occur in the anolyte compartment 208. Specifically, a photolysis device 410 is designed such that it may emit (irradiate) radiation 412 into the anolyte compartment 208. This irradiation may produce hydrogen radicals (H.). The hydrogen gas 320 may be supplied to the anolyte compartment 208 using any of the mechanisms described above, as illustrated by the following equation:

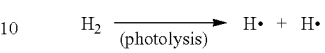

This photolysis process may be combined with the electrolysis process of the cell described above:

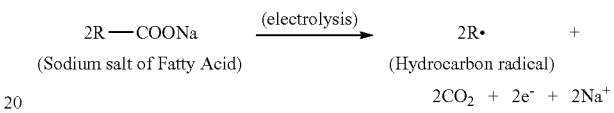

The hydrogen radicals and the hydrocarbon radicals may then combine to form a mixture of products:

2H.+2R.→H—R+R—R+$H_2$

Alternatively, the photolysis device may be used to conduct decarboxylation and to generate hydrocarbon radicals:

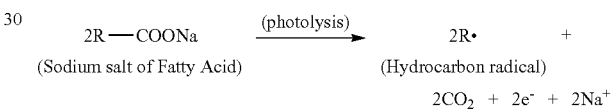

Thus, a combination of photolysis and electrolysis may be used to form the hydrocarbon radicals and/or hydrogen radicals in the anolyte compartment 208:

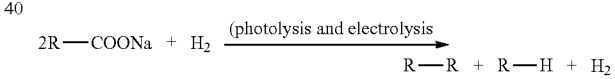

This combination of electrolysis and photolysis may speed up the rate of the decarboxylation reaction.

Yet additional embodiments may be designed using such photolysis techniques. For example, the following reactions may occur:

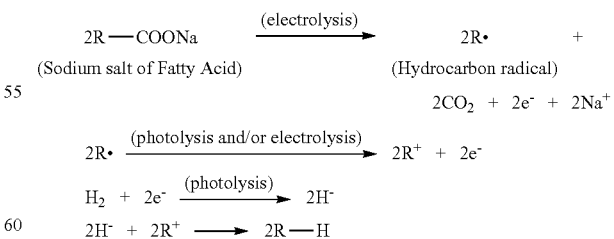

This combination of reactions (using photolysis and electrolysis) forms carbocations and $H^-$ anions that may combine to form the hydrocarbon. Thus, photolysis may be used as a further mechanism for forming hydrocarbons. As has been discussed above, although hydrocarbons are being used in these examples, the coupled radical product need not be a hydrocarbon. In certain embodiments, the method and apparatus of the present invention may be used to create nonhydrocarbon radicals which may couple together to form useful coupled radical products.

Referring now to FIGS. 2-4 collectively, it is noted that each of these illustrative embodiments involve separation of the anolyte compartment 208 and the catholyte compartment 204 using the membrane 212. As described herein, specific advantages may be obtained by having such a membrane 212 to separate the anolyte compartment 208 from the catholyte compartment 204. These advantages include:

- two separate environments for different reaction conditions—for example, the anolyte may be non-aqueous, while the catholyte is aqueous (and vice versa);
- anolyte may be at a higher temperature than the catholyte (and vice versa);
- anolyte may be pressurized and catholyte not (and vice versa);
- anolyte may be irradiated and catholyte not (and vice versa);
- anolyte and/or anode may be designed to conduct specific reactions that are not dependent upon the catholyte and/or cathode reactions (and vice versa);
- the different chambers may have different flow conditions, solvents, solubilities, product retrieval/separation mechanisms, polarities, etc.

The ability to have separate reaction conditions in the anolyte compartment and catholyte compartment may allow the reactions in each compartment to be tailored to achieve optimal results.

Likewise, a membrane, comprising, for example, NaSICON, has a high temperature tolerance and thus the anolyte may be heated to a higher temperature without substantially affecting the temperature of the catholyte (or vice versa). (NaSICON can be heated and still function effectively at higher temperatures). This means that polar solvents (or non-polar solvents) that dissolve fatty acids and sodium salts at high temperatures may be used in the anolyte. For example, palmitic acid may be heated to form a liquid and this liquid is an excellent solvent for sodium palmitate. At the same time, the catholyte is unaffected by temperature. In fact, a different solvent system could simultaneously be used in the catholyte. Alternatively, other molten salts or acids may be used to dissolve ionic sodium carboxylic acids and salts in the anolyte. Long chain hydrocarbons, ethers, triglycerides, esters, alcohols, or other solvents may dissolve carboxylic acids and sodium salts. Such compounds could be used as the anolyte solvent without affecting the catholyte. Ionic liquids could be used as the anolyte solvent. These materials not only would dissolve large quantities of fatty acid sodium salts, but also, may operate to facilitate the decarboxylation reaction at higher temperatures. Ionic liquids are a class of chemicals with very low vapor pressure and excellent dissolving abilities/dissolving properties. A variety of different ionic liquids may be used.

Figure 5:
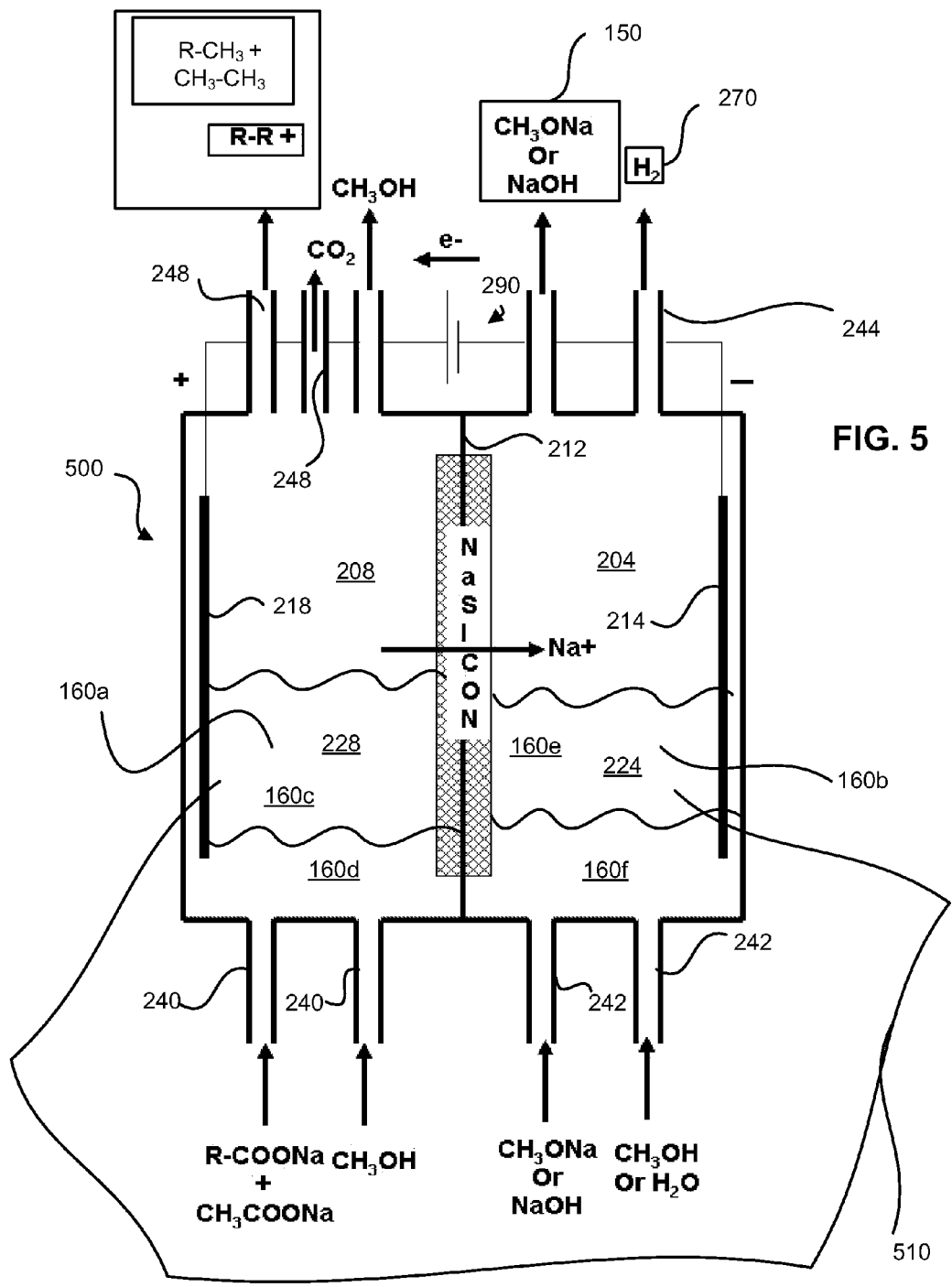
FIG. 5 is a schematic view of another embodiment of an electrolytic cell for conversion of sodium salts of fatty acids to coupled radical products.

Referring now to FIG. 5, another embodiment of a cell 500 is shown. This cell 500 is similar to that which is described above in conjunction with the other Figures. Accordingly, for purposes of brevity, this description will not be repeated, but is incorporated by reference herein.

As explained above, one of the advantages of the present cell is that it produces a base 150 in the catholyte compartment 204. As noted above, this base 150 may then be used as part of the saponification reaction 121 that produces the sodium salt of the fatty acid. In the context of FIG. 5, this regeneration of the base 150 occurs via the following reaction:

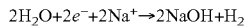

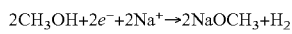

The Na⁺ ions for this reaction come from the anolyte 228. Specifically, the sodium ions migrate through the membrane 212 as shown by FIG. 5. The base 150 produced in such reactions is either NaOH or NaOCH₃ which may be recycled and used in the saponification reactions.

Alternatively, embodiments may be made in which the fatty acids may be saponified directly in the catholyte compartment 208. In other words, the saponification reaction 121 occurs within the cell itself to produce the fatty acid sodium salt, and this sodium salt is then taken from the catholyte compartment 204 to the anolyte compartment 208 (such as via conduit 510). Fatty acid is added to the catholyte 224 and may react (saponified) as follows:

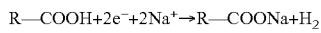

This R—COONa is the sodium salt of the fatty acid 108, which is then introduced into the anolyte compartment 208 either through a conduit 510 (or perhaps through an inlet 240). This sodium salt would then be reacted (decarboxylated), forming coupled radical products such as hydrocarbons. This process thus allows the fatty acid to be saponified in situ (e.g., within the cell). This process would be a one step process (e.g., simply running the cell) rather than a two step process (saponification and decarboxylation within the cell).

Triglycerides may also be saponified as used in the present processes. Such saponification may occur within the cell 500 or exterior of the cell. Such saponification of triglycerides may occur, for example, as follows:

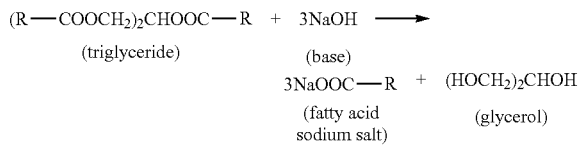

If sodium methoxide (or another organic base) is used rather than sodium hydroxide, the reaction with a triglyceride may be as follows:

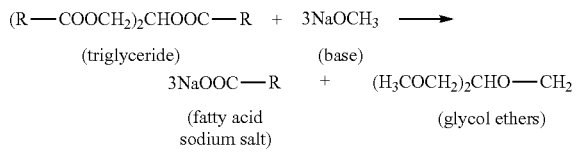

Referring now to FIGS. 2-5, it is apparent that the present embodiments allow for a ready separation of the produced hydrocarbon material in the anolyte compartment 208. This may occur by having the anolyte compartment 208 include a mixture of solvents 160. For example, the solvent may comprise an organic phase solvent (such as a non-ionic, non-aqueous solvent). (Inorganic or other solvents may also be used.) An example of such a solvent would be a long chain fatty acid alcohol, or other similar organic solvent. Mixed with this organic phase solvent is an ionic solvent or aqueous solvent, such as water or an ionic liquid. This water/ionic liquid dissolves the sodium salt of the fatty acid. This two-phase solvent system is shown in FIG. 5. Specifically, the first solvent 160a comprises a mixture of a first phase solvent 160c (such as an aqueous phase) and a second phase solvent 160d (such as an organic solvent) Likewise, the second solvent 160b comprises a mixture of a first phase solvent 160e (such as an aqueous phase) and a second phase solvent 160f (such as an organic solvent).

Using this type of "two-phase" system, the hydrocarbon, when formed, will readily dissolve in the organic phase, and will be repelled by the aqueous/ionic phase. This means that the formed hydrocarbon(s) will readily separate from the aqueous/ionic phase. The reaction may be summarized as follows:

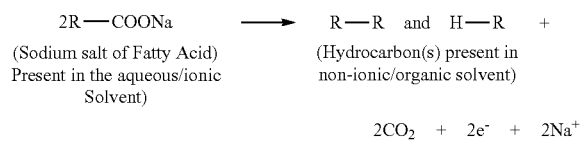

Similar separation may be obtained by using two solvents of different polarities as well. Another example of this principle involves glutaric acid. Sodium glutarate is not soluble in methanol, but is soluble in water. Accordingly, if water is used as one of the solvents in a two-phase system, it will dissolve the sodium glutarate. Another non-polar and/or organic solvent is used with water. When the hydrocarbon is formed, this hydrocarbon is not soluble in water. Rather, the hydrocarbon will dissolve into the non-polar/organic solvent. The reactions associated with this example are provided below:

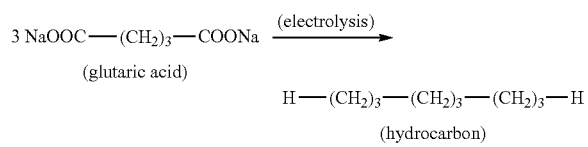

This hydrocarbon $H-(CH_2)_3-CH_{2)3}-CH_2)_3-H$ is non-polar and will migrate to the non-polar/organic solvent. Also, the non-polar nature of the solvent may also operate to terminate the reaction so that a product with nine carbon atoms forms, rather than allowing a larger polymer to form (by repeated addition of the $-(CH_2)_3-$ monomer unit). Thus, by selecting the particular solvent, the reaction conditions for a di-, tri-, or polycarboxylic acid may be tailored to produce a specific product. This use of organic or inorganic solvents may also be applied to the catholyte in a similar manner.

In one embodiment, the anolyte comprises G-type solvents, H-Type solvents, and/or mixtures thereof. G-type solvents are di-hydroxyl compounds. In one embodiment the G-type compound comprises two hydroxyl groups in contiguous position. H-type solvents are hydrocarbon compounds or solvent which can dissolve hydrocarbons. For example, H-type solvents include, hydrocarbons, chlorinated hydrocarbons, alcohols, ketones, mono alcohols, and petroleum fractions such as hexane, gasoline, kerosene, dodecane, tetrolene, and the like. The H-type solvent can also be a product of the decarboxylation process recycled as a fraction of the hydrocarbon product. This will obviate the need of procuring additional solvents and hence improve overall economics of the process.

By way of further description, G-type of solvents solvate a $-COONa$ group of a alkali metal salt of carboxylic acid by hydrogen bonding with two different oxygen atoms, whereas the hydrocarbon end of the alkali metal salt of carboxylic acid is solvated by an H-type of solvent. For a given G-type solvent, the solvency increases with increase of hydrocarbons in the H-type solvent.

The table below shows some non-limiting examples of G-type and H-type solvents:

| G-type | H-type |
| --- | --- |
| ehthylene glycol | isopropanol |
| glycerine | methanol |
| 1,2-dihidroxy-4-oxadodecane | ethanol |
| 2-methyl-2-propyl-1,3-propanediol | butanol |
| 2-ethyl-1,3-hexanediol | amyl alcohol |
| 2-amino-2-methyl-1,3-propanediol | octanol |
| 2,3-butanediol | hexane |
| 3-amino-1,2-propanediol | trichloroethane, dichloroethane |
| 1,2-octanediol | methylene dichloride |
| cis-1,2-cyclohexanediol | chloroform |
| rans-1,2-cyclohexanediol | carbon tetrachloride |
| cis-1,2-cyclopentanediol | tetralin |
| 1,2-pentanediol | decalin |
| 1,2-hexanediol | monoglyme |
| | diglyme |
| | tetraglyme |
| | acetone |
| | acetaldehyde |

The solubility of various sodium salts of carboxylic acids were tested at room temperature in a magnetically stirred glass beaker using G-type solvents, H-type solvents, and combinations of G- and H-type solvents. The following tables show solubility test results for various salts.

| Salt: Sodium Oleate | | |
| --- | --- | --- |
| Solvent/Co-solvents | Solubility | Solubility limit g/100 g |
| Ethylene glycol | ✓ | 36.00 |
| Ethylene glycol/Isopropanol (1.4:1) | ✓ | 57.90 |
| Ethylene glycol/Methanol (1.4:1) | ✓ | 31.25 |
| Ethylene glycol/Methanol (5.55:1) | ✓ | 9.56 |
| Methanol | ✓ | 16.60 |

| Salt: Sodium Stearate | | |
| --- | --- | --- |
| Solvent/Co-solvents | Solubility | Solubility limit g/100 g |
| Ethanol | x | |
| Ethylene glycol | x | |
| Ethylene glycol/Butanol (1:1) | ✓ | 4.66 |
| Ethylene glycol/Isopropanol (1.4:1) | ✓ | 0.35 |
| Isopropanol | x | |
| Methanol | x | |
| Octanol | x | |

| Salt: Sodium Palmitate | | |
|---|---|---|
| Solvent/Co-solvents | Solubility | Solubility limit g/100 g |
| Acetone | x | |
| Butanol | x | |
| Ethanol | x | |
| Ethanol/Hexane (1:1) | x | |
| Ethylene glycol | x | |
| Ethylene glycol/Butanol/Isopropanol (1:1:1) | x | |
| Ethylene glycol/Butanol/Methanol (1:1:1) | x | |
| Ethylene glycol/Butanol (1:1) | ✓ | 18.00 |
| Ethylene glycol/Butanol/Methanol/Isopropanol (1:1:1:1) | x | |
| Ethylene glycol/Ethanol (1:1) | ✓ | 4.66 |
| Ethylene glycol/Ethanol/Methanol/Isopropanol (1:1:1:1) | ✓ | 2.11 |
| Ethylene glycol/Isopropanol (1.4:1) | x | |
| Ethylene glycol/Methanol (1:1) | ✓ | 5.26 |
| Ethylene glycol/Methanol/EMIBF4 (2:2:1) | x | |
| Ethylene glycol/Methanol/EMIBF4/BMIBF4 (2:2:1:1) | x | |
| Ethylene glycol/Methanol/Isopropanol (1:1:1) | ✓ | 5.10 |
| Hexane | x | |
| Hexane/Ethylene glycol (2:1) | x | |
| Isopropanol | x | |
| Methanol | ✓ | 0.80 |
| Octanol | x | |

It should be noted that although there are specific advantages of using a divided cell, embodiments may be constructed in which the cell is undivided. This cell may be summarized as follows:

Pt||R—COONa+CH$_3$ONa+CH$_3$OH||Pt

The Pt electrodes may be replaced by other electrodes, as outline herein. Also, the sodium methoxide base (CH$_3$ONa) may be replaced by other bases (such as hydroxide, sodium methylate, or other bases), as desired. Likewise, the solvent, methanol (CH$_3$OH), may be replaced by other solvents, as desired. In this embodiment, the anode reaction is a decarboxylation reaction to form carbon dioxide and R—R. The cathode reaction is a reduction to form hydrogen gas (the H being provided by the methanol). In other embodiments, acetate (or other carboxylic acid anions) may optionally be used. Similarly, the acidic form of the sodium salt may be used, provided that there is also base to convert it to a sodium salt.

Although many of the examples provided herein involve the use of monocarboxylic acids, dicarboxylic acids or polycarboxylic acids may also be used. However, when using dicarboxylic acids or polycarboxylic acids, steps (in some embodiments) may be taken to avoid or reduce polymerization. This polymerization reaction is summarized below by a dicarboxylic acid, but a similar reaction is possible for a polycarboxylic acid:

NaOOCR—RCOONa $\xrightarrow{\text{(decarboxylation)}}$ ·R—R·

(sodium salt of a dicarboxylic acid)

Since these hydrocarbon radicals have reactive sites at each end, these .R—R. radicals could then line up to polymerize:

. . . .R—R.+.R—R..R—R.+.R—R. . . .

In some embodiments, such polymerization may be desired. In other embodiments, polymerization is not desired. Accordingly, techniques may be employed to reduce the likelihood of polymerization (e.g., "cut off" the polymerization). This may involve, for example, forming methyl radicals (CH$_3$.) via acetate, forming H. radicals to truncate the R group. Likewise, the techniques associated with using a mixed solvent system may also reduce such polymerization. For example, by using a nonpolar solvent in combination with a polar solvent in the anolyte, the formed hydrocarbon will be pulled into the non-polar solvent quickly, thereby preventing it from polymerizing.

Various examples of the techniques described herein may be used and performed readily. Some of these examples include:

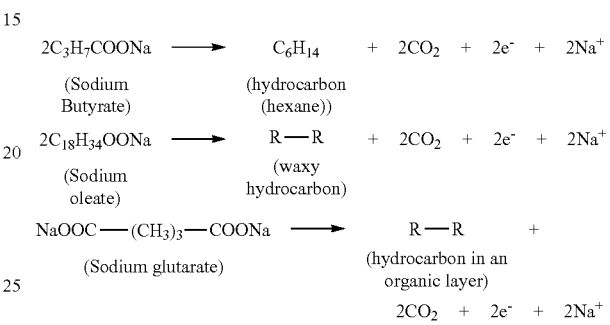

Figure 6:
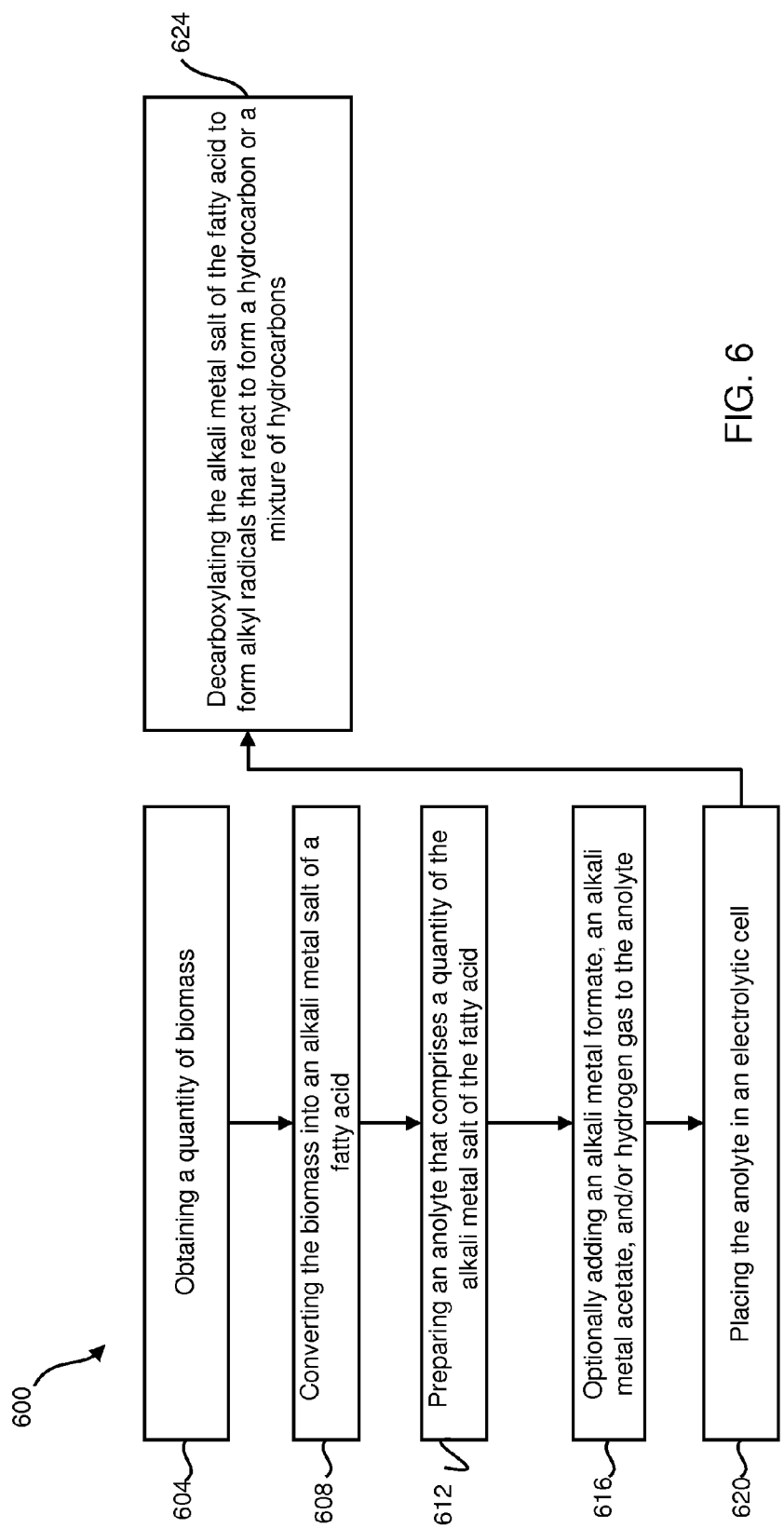
FIG. 6 is a flow diagram showing one embodiment of a process of forming a hydrocarbon.

(Sodium Oleate and Sodium linolate) obtained from soybean oil, and acetate mixture C$_{17}$H$_{33}$COONa+C$_{17}$H$_{31}$COONa+CH$_3$COONa →mixture of products including C$_{17}$ and C$_{18}$ hydrocarbons A number of different methods may be employed to form coupled radical products within the scope of the present disclosure. For example, FIG. 6 shows an embodiment of a method 600 that may be used to form a hydrocarbon or a mixture of hydrocarbons. The method involves obtaining 604 a quantity of biomass. The biomass may, in one embodiment, be obtained from any source, such as from algal, plant, microbes, microorganisms, and animals. Once obtained, the biomass is converted 608 into at least one alkali metal salt of a fatty acid. FIG. 1 shows a variety of different methods, procedures, reactions, and steps that may be used to convert the biomass into at least one alkali metal salt of a fatty acid. Any and/or all of these steps may be used. An anolyte will then be prepared 612. The anolyte comprises a quantity of the alkali metal salt of the fatty acid. The methods and ingredients outlined herein describe how this anolyte may be prepared. Optionally, an alkali metal formate, an alkali metal acetate, and/or hydrogen gas may be added 616 to the anolyte. Once prepared, the anolyte may be placed 620 in an electrolytic cell, such as those described herein.

After placing the anolyte in the cell, the alkali metal salt of the carboxylic acid is decarboxylated 624. This decarboxylation may involve electrolysis and/or photolysis. Such decarboxylation forms one or more radicals that react to form a coupled radical product such as hydrocarbon or a mixture of hydrocarbons. These hydrocarbons may then be collected, purified (as needed) and/or used in industry.

Figure 7:
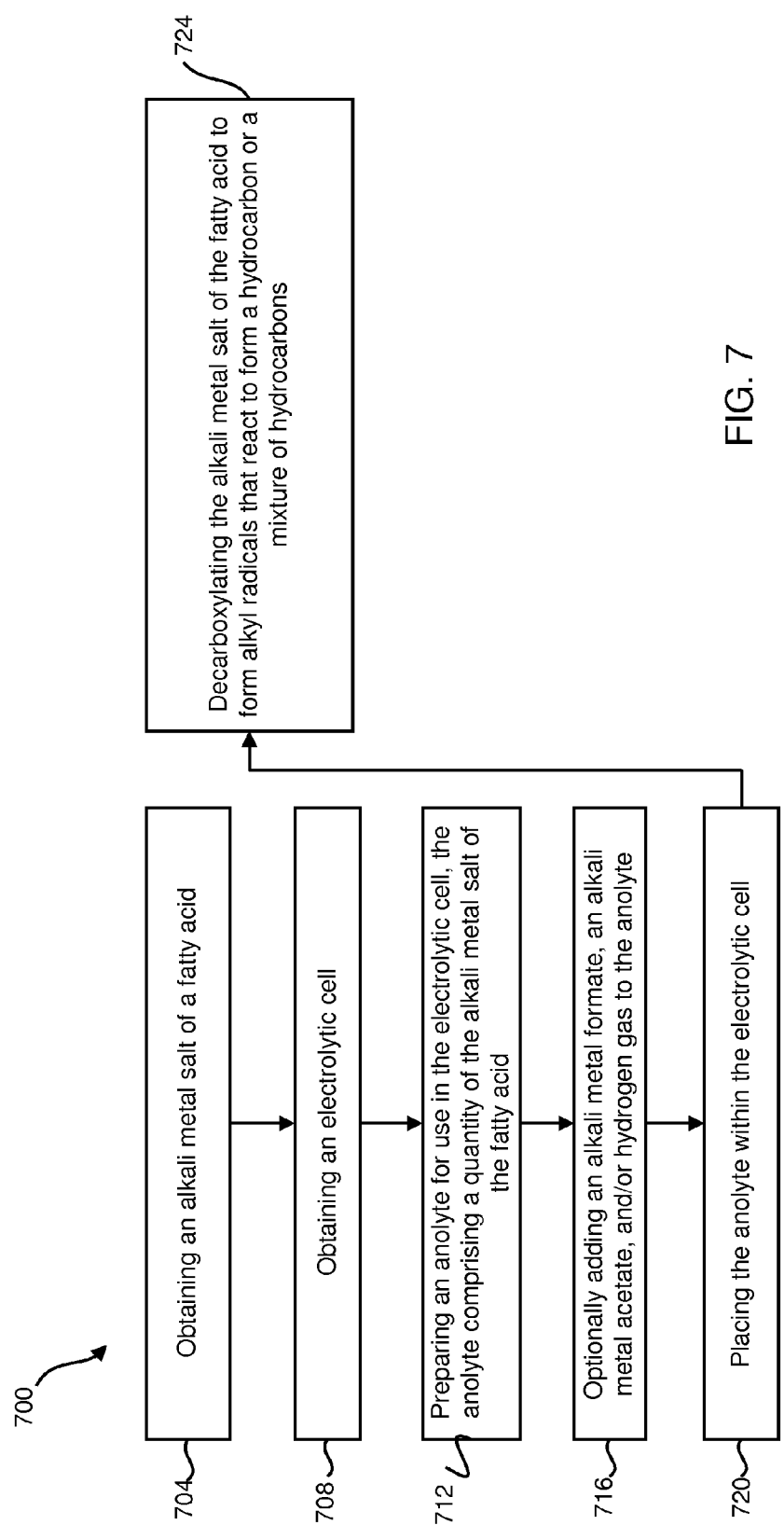
FIG. 7 is a flow diagram showing another embodiment of a process of forming a hydrocarbon.

FIG. 7 is a flow diagram showing another method 700 for producing a coupled radical product. In one embodiment, the method 700 comprises obtaining 704 an alkali metal salt of a fatty acid. As noted herein, this alkali metal salt of a fatty acid may be derived from biomass. Alternatively, this alkali metal salt of the fatty acid may be purchased or otherwise obtained. The alkali metal salt of the fatty acid may be a sodium salt.

The alkali metal salt of the fatty acid may be derived from fatty acids (such as dicarboxylic acids, monocarboxylic acids, and/or polycarboxylic acids), esters of fatty acids, triglycerides of fatty acids, carbohydrates, fatty acid derivatives, and/or metal salts of fatty acids.

An electrolytic cell will also be obtained 708. An anolyte is also prepared 712. The anolyte may be of the type described herein. The anolyte comprises a quantity of the alkali metal salt of the fatty acid. A quantity of an alkali metal acetate, a quantity of hydrogen gas, and/or a quantity of an alkali metal formate may optionally be added 716 to the anolyte. The anolyte may be placed 720 in the electrolytic cell.

The anolyte is electrolyzed 724 within the cell. This electrolyzing operates to decarboxylate the alkali metal salt of the fatty acid to form alkyl radicals. These alkyl radicals react to form a hydrocarbon or a mixture of hydrocarbons. These hydrocarbons may then be collected, purified (as needed) and/or used in industry.

Further embodiments may be employed in which the anolyte includes a mixture of a fatty acid (R—COOH) and an alkali metal salt of a fatty acid (R—COO—AlMet). As described above, this anolyte (including the mixture of the fatty acid and the alkali metal salt of the fatty acid) is fed into a compartment (such as the anolyte compartment 208) in which decarboxylation will occur.

When this mixture is decarboxylated, embodiments may be designed in which only the alkali metal salt of the fatty acid will decarboxylate and not the fatty acid. The alkali metal salt of the fatty acid (R—COONa) is more polar than the fatty acid (R—COOH) and thus, the alkali metal salt of the fatty acid is more likely to decarboxylate at lower voltages. Thus, by selecting a lower applied voltage, embodiments may be constructed in which only the alkali metal salt of the fatty acid decarboxylates and not the fatty acid.

When the alkali metal salt of the fatty acid (R—COONa) decarboxylates, it creates an alkyl radical:

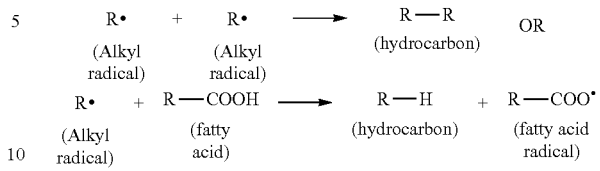

In turn, this alkyl radical (R.) can extract a hydrogen radical (H.) from the fatty acid in the anolyte:

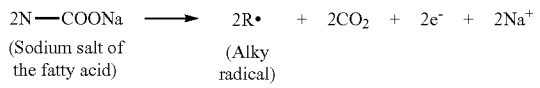

As can be seen from this reaction, a R—H hydrocarbon is obtained. This reaction may not create a dimer hydrocarbon product (R—R). At the same time, the formed fatty acid radical (R—COO.) can also decarboxylate under the applied electric potential:

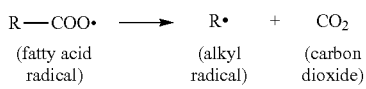

This formed alkyl radical (R.) will itself react, either by reacting with another alkyl radical (R.) to form the (dimer) hydrocarbon R—R, or by extracting a hydrogen radical from the fatty acid to create another fatty acid radical (RCOO.). These two reactions are summarized below:

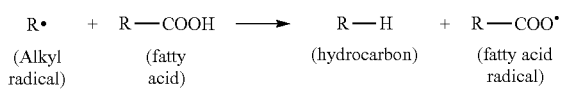

As can be seen from these reactions, the reaction continues to product fatty acid radicals (RCOO.) as it is being consumated and these R—COO. radicals may continue to react in the manner described herein. This reaction is therefore characterized as a free radical "chain reaction." This chain reaction will continue to react until the fatty acid supply in the anolyte is exhausted, at which point the alkyl radical (R.) will react with another alkyl radical (R.) to create the R—R hydrocarbon. Alternatively, the reaction may be quenched using other techniques.

By using a free radical chain reaction, the reaction will be naturally driven on its own once started. An electric potential (or electric current or perhaps irradiation) is needed to start (initiate) the reaction. However, once started, the voltage/current (potential or perhaps the radiation) needed to continue the reaction become smaller (or perhaps even zero). This decrease in the required current/voltage/radiation needed to run the reaction decreases the costs associated with conducting the reaction.

An additional application for the present embodiments may be in the field of bio-diesel synthesis. During some currently used bio-diesel synthesis processes, vegetable oil is reacted with methanol in the presence of a sodium methylate catalyst in order to form the bio-diesel product. This bio-diesel product is a methyl ester. During this synthesis process, there are two phases produced, namely an upper phase and a lower phase. The "upper" phase is the non-polar phase and contains the methyl ester (bio-diesel product). The "lower" phase is the polar phase and includes methanol, glycerol, and the products of the vegetable oil, namely, fatty acids (or sodium salts of fatty acids), and/or other sodium salts (such as sodium chloride or sodium sulfate, etc.). This lower phase can contain, in some embodiments, nearly 20% fatty acid (by weight). In some bio-diesel synthesis processes, there is a large amount of this lower phase produced, and thus this "lower phase" material is readily available. Accordingly, if the lower phase is obtained, it could be directly fed into a cell of the type that is described herein. Alternatively, the lower phase may be pre-processed through additional reactions (such as saponification or other reactions to increase the content of the sodium salt of the fatty acid). This lower phase could be decarboxylated in a cell having a NaSICON membrane, thereby producing a hydrocarbon (and more particularly a methyl ester) that is non-polar. This produced hydrocarbon/methyl ester product could be used as a new "upper phase" for further processing and/or may be the desired bio-diesel fuel product itself. Thus in a NaSICON cell, it may be possible to recover and/or re-use the fatty acid in the bio-diesel process, thereby making the process more cost-efficient and environmentally-friendly. This process may also remove the sodium salts from the lower phase.

NON-EXCLUSIVE EXAMPLES

Below is listed some examples of embodiments described herein. These embodiments are not to be construed as being limiting but are exemplary.

Preparation:

Due to the changing composition of commercially available mixtures of fatty acids, surrogates (mixtures of fatty acids) were used as starting materials for some of the reactions. Accordingly, the following surrogates were prepared and/or purchased:

1) sodium oleate
2) sodium oleate & sodium linoleate, and
3) sodium oleate, sodium linoleate, sodium palmitate & sodium stearate.

In some situations, the sodium salts of the fatty acid were directly purchased and mixed to make the surrogates. In other situations, the fatty acids were purchased and converted into the corresponding sodium salts by a saponification reaction using 12-15% sodium methylate/methanol.

The appropriate solvent(s) available for the reactions was first investigated to determine a solvent that may effectively solubilize the fatty acids and is also highly conductive. Solvents were considered based upon their ability to form highly concentrated anolyte solutions with the selected acid starting materials. Both single phase and multi phase solvent mixtures were considered. The following solvents were considered based on one or more of the following factors: (1) high solubility at low temperatures, (2) liquids at room or low temperatures, (3) low viscosity, (4) cost, and (5) ease of product separation. Based on the above criteria, the following solvents were identified for Sodium Oleate & Linoleate: (1) Methanol, and (2) Isopropanol+Ethylene glycol. For a mixture of Sodium Oleate, Linoleate, Palmitate and Stearate, appropriate solvent systems were: (1) Butanol+Ethylene glycol, (2) Methanol+Ethanol+Isopropanol+Ethylene glycol. Once these solvents had been determined, anolytes were prepared by dissolving sodium fatty acids in minimal amount of selected solvent system.

The sodium salt solutions that were prepared had low conductivity, because of the limited number of sodium ions (when compared to a conductive solution such as brine or NaOH). Therefore, a supporting electrolyte that is electrochemically inert to the anolyte was added for solution conductivity purposes and to achieve a low operational voltage. Tetraethylammonim tetrafluoroborate was chosen as the supporting electrolyte based on its cost, high solubility in the solvent systems, and its large electrochemical stability window.

A two compartment micro-reactor with a small gap between the ion-conducting membrane and the anode was fabricated and used in the decarboxylation process. The small (minimal) gap was chosen to create optimum mass transfer conditions in the anolyte compartment. A smooth platinum anode was used where decarboxylation occurs. A 1" diameter and 1 mm thick NaSelect ion-conducting membrane (available from Ceramatec, Inc., of Utah) was used between the anode and cathode compartment. A nickel cathode was used in the cathode compartment. A 1 liter glass flask sealed with 3-holed rubber stoppers was used. The appropriate anolyte and catholyte reservoirs were prepared and connected to the sealed flask. Each reservoir was placed on a hot plate and thermocouples were placed in each of the reservoirs. About 300 mL of anolyte and catholyte (15 wt. % NaOH) were used. The temperature was controlled by a temperature controller to maintain the temperature of feed solutions to the anolyte, and catholyte at 40 to 60° C. Peristaltic pumps were used to circulate the solutions at flow rate of 60 to 100 mL per minute (depending on the viscosity). Lab view data acquisition was used to measure the voltage and current. The carbon dioxide evolved from the anolyte was fed into a $CO_2$ IR sensor (Detcon) where the wt. % of $CO_2$ was qualitatively determined.

The electrolysis reactor was operated in batch mode. Batch mode means that the anolyte and catholyte were re-circulated until majority of the sodium salts were converted to hydrocarbons in the anolyte and the majority of the sodium ions were transferred to the catholyte compartment via the membrane formed sodium hydroxide in the catholyte (where aqueous sodium hydroxide is concentrated). Alternatively, the electrolysis reactor was also operated in semi-continuous mode, i.e., the anolyte and catholyte were re-circulated until a pre-determined amount of sodium salts starting material (e.g., 10%) was converted to hydrocarbons in the anolyte. The reactors were operated at constant current densities ≥50 mA/cm$^2$ to 200 mA/cm$^2$ of membrane area. A continuous process may be preferred for large-scale processing in which the starting salt concentration is always maintained and the hydrocarbon product is continuously removed.

The hydrocarbon product from the anolyte was at times recovered using a solvent immiscible with the starting solvent mixture. Hexane and Dodecane were the choices for hydrocarbon product recovery. The hexane or dodecane phase was analyzed by GC (gas chromatography) or GC-MS (gas chromatography-mass spectrometry) analysis for the estimation of product. In some cases for quantification purpose, the starting anolyte and final anolyte were submitted without extraction with hexane or dodecane.

Test #1

Decarboxylation of sodium oleate. Sodium oleate was dissolved in a methanol solvent. The purpose of this test was to determine the product conversion efficiency in a semi-continuous mode of operation. The test was conducted at a constant current density of 200 mA/cm$^2$ until about 50% of starting material was theoretically converted.

The GC profile for the reacted anolyte is shown in Table 1. Table 1 shows the major peaks, name of the chemical identified, retention time in minutes, height in microvolts, area under the curve in (μV.Min) and % area under curve. The peaks at retention time at 18.65 and 27.36 are tentatively identified as sodium oleate (C18) and C34 hydrocarbon dimer. The area under the curve for C18 peak before and after the test was compared to determine the conversion efficiency. The product conversion efficiency based on this analysis was nearly 80%.

TABLE 1

| Index | Name | Time [Min] | Height [mV] | Area [mV.Min] | Area % |
|---|---|---|---|---|---|
| 1 | Methanol | 1.77 | 24812452.2 | 629819 | 88.145 |
| 2 | Acetone | 1.86 | 639511.8 | 19623.4 | 2.746 |
| 3 | Unknown | 18.65 | 497370.5 | 49679.9 | 6.953 |
| 4 | Unknown | 27.36 | 252032.9 | 15407.3 | 2.156 |

ICP (inductively coupled plasma) analysis of the reacted liquid sample showed that 51% of the sodium was removed from the anolyte. The sodium transport current efficiency was determined to be 99%.

Test #2

Figure 8:
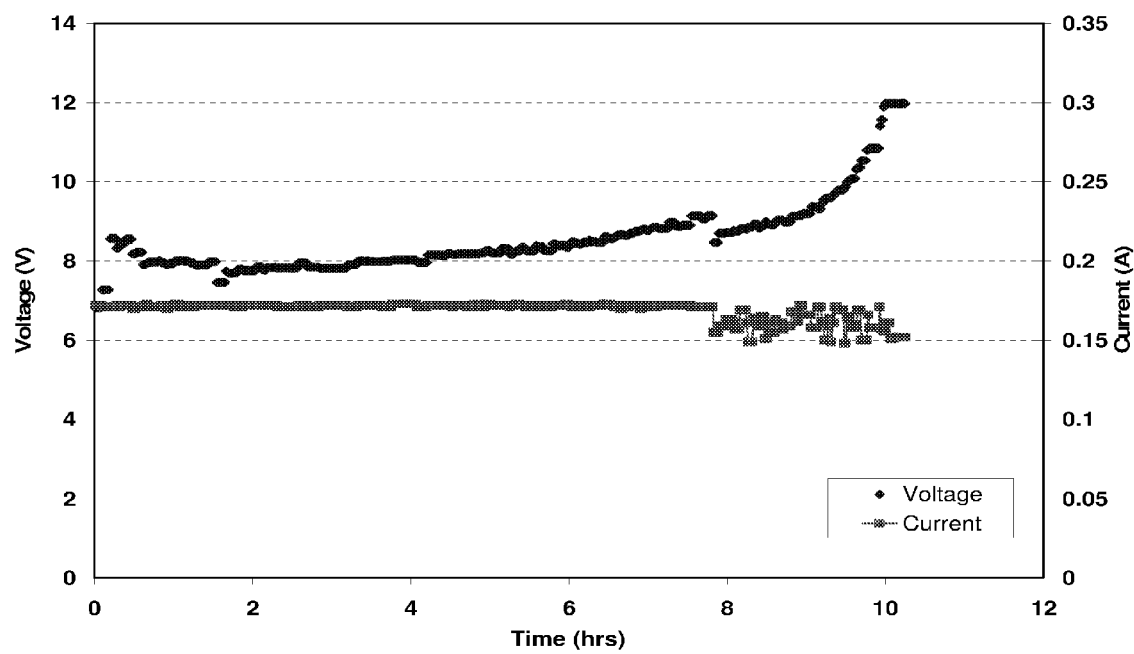
FIG. 8 is a graph of voltage versus time during the decarboxylation of an anolyte according to the present embodiments.

Decarboxylation of a mixture of sodium oleate and sodium linoleate. Sodium oleate and sodium linoleate was dissolved in a methanol solvent. The purpose of the test was to determine the reactor power consumption and to determine a current-voltage profile when the reactor was operated in batch mode. The test was conducted at a constant current density of 50 mA/cm$^2$ until a preset voltage limit of 12 volts was reached. FIG. 8 shows the voltage data for test 2. The data showed a steady low voltage of 8V during much of the test and steep voltage increase during later part of the test, due of the depletion of sodium in the anolyte. ICP analysis of the reacted anolyte sample showed that 87% of the sodium was removed from the anolyte (initial and final sodium contents from ICP are 16,000 mg/L and 2,400 mg/L respectively). The sodium transport current efficiency was determined to be 95.5% and the power consumption was determined to be 0.95 kWh/kg of hydrocarbon produced (based on calculation that every two sodium ions removed will create a molecule of hydrocarbon). GC analysis showed the presence of fatty acid methyl ester peaks along with hydrocarbon peaks. It appears from the data that there is high sodium transfer (current) efficiency with low average voltage of 8.54 V and low power consumption.

Figure 9:
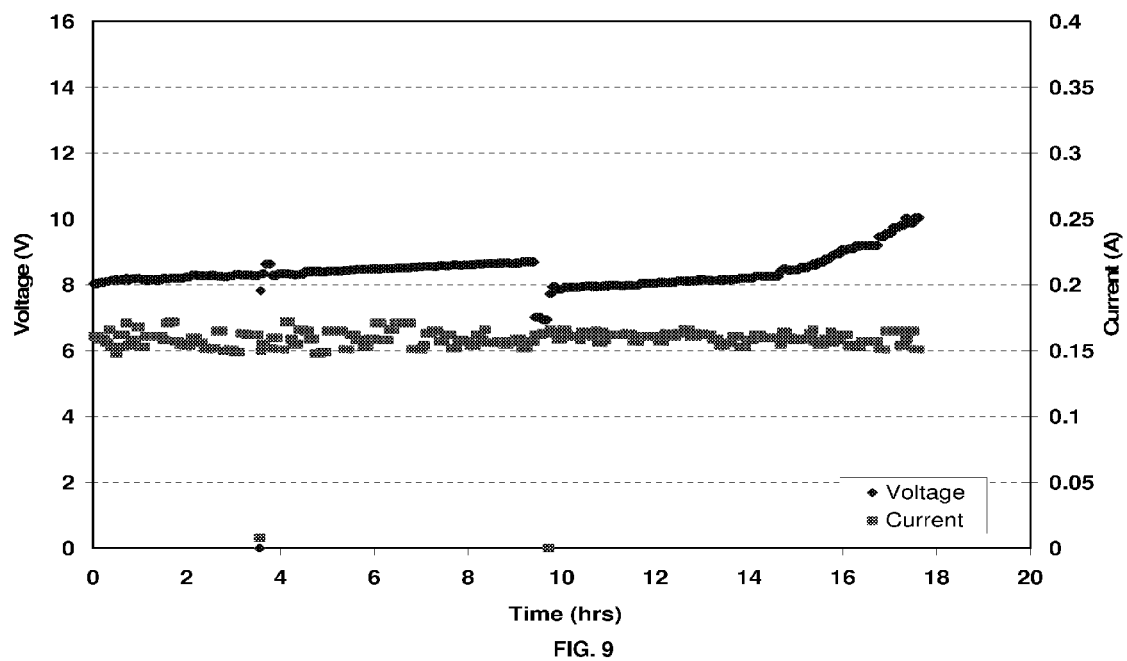
FIG. 9 is a gas chromatagraph printout showing an anolyte that has been reacted according to the present embodiments.

Decarboxylation of a mixture of sodium oleate, sodium linoleate, sodium palmitate and sodium sterate. Sodium oleate, sodium linoleate, sodium palmitate and sodium sterate were dissolved in a four solvent mixture of Methanol/Ethanol/Isopropanol/Ethylene Glycol. The purpose of the test was to determine the current-voltage profile when the reactor is operated in batch mode. The test was conducted at a constant current density of 50 mA/cm$^2$ for about 18 hours. FIG. 9 shows the voltage data for test 3. The voltage data shows a break at about the 9$^{th}$ hour, due to an overnight shutoff of the reactor. The data shows a steady low voltage of 8V during much of the test and steep voltage increase during later part of the test because of the exhaustion of the reactant. The data shows an average voltage of about 8.37 V.

Test #4:

This test used an anolyte with the same composition as in Test #2 (sodium oleate and sodium linoleate dissolved in a methanol containing 10% water). The purpose of this test was to determine the product conversion efficiency in a continuous mode of operation while eliminating the formation of fatty acid esters during decarboxylation process. The test was conducted at a constant current density of 200 mA/cm$^2$ (4 times higher than test #2 but equal to the current density of test #1) for a short period. The Gas Chromatogram (GC) profile for the reacted anolyte showed only hydrocarbons as the products. Thus it appears that operation at high current density may be employed, for some embodiments, to produce the hydrocarbons.

It has also been determined that the production of hydrocarbons, could in some embodiments, be economically feasible. For example it has been estimated that using a continuous mode processing, 1 gallon of hydrocarbon could be made for between $0.798 to $0.232.

Accordingly, the foregoing examples indicate the following:

Conversion of sodium salts of fatty acids to >C30 hydrocarbons was achieved;
Mixtures of sodium salts of fatty acids were converted to hydrocarbons;
Additives were used to assist in lowering the decarboxylation reactor voltage at high operational current densities;
Nearly 80% product conversion efficiency was achieved for a sodium oleate conversion;
Greater than 90% product conversion efficiency was achieved for conversion of a sodium oleate/sodium linoleate mixture (during continuous mode operation);
An NaSelect ion-conducting membrane (available from Ceramatec, Inc. of Utah) operated at near 100% sodium ion transfer efficiency;
Approximately 90% of sodium ions was transferred to the catholyte compartment to form sodium hydroxide at a low operational voltage;
The power consumption was observed to be 0.95 kWh/kg of hydrocarbon processed;
The selectivity for forming hydrocarbons may be improved by operating the reactor at high current density; and
The presence of water may help the selectivity towards hydrocarbon formation.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

The invention claimed is:

1. A method for producing a coupled radical product from biomass comprising:
    providing an electrolytic cell comprising an anolyte compartment having an anode and housing an anolyte, a catholyte compartment having a cathode and housing a catholyte, and a NaSICON membrane separating the anolyte compartment and the catholyte compartment;
    obtaining a quantity of a biomass comprising a lipid;
    converting the lipid into a fatty acid by one or more of hydrolysis, fermentation, and saponification;
    saponifying the fatty acid to produce a sodium metal salt of the fatty acid, wherein the sodium metal salt of the fatty acid has a number of carbon atoms and wherein saponifying the fatty acid occurs in the catholyte compartment and comprises reacting a base produced by electrolysis from the catholyte with a quantity of the fatty acid to produce the sodium metal salt of the fatty acid;
    wherein the anolyte comprises a quantity of the sodium metal salt of the fatty acid and at least one G-type solvent and at least one H-type solvent;
    adding to the anolyte, a quantity of a supporting electrolyte comprising a sodium salt of a lower alkyl carboxylic acid, wherein the sodium salt of the lower alkyl carboxylic acid is selected to have a predetermined number of carbon atoms; and
    decarboxylating the sodium metal salt of the fatty acid within the anolyte, wherein the decarboxylating step occurs by electrolysis within the anolyte compartment and converts the sodium metal salt of the fatty acid into at least one alkyl radical and converts the supporting electrolyte into a lower alkyl radical or to a hydrogen radical that react to form a hydrocarbon coupled radical product comprising a hydrocarbon having a total number of carbon atoms based upon the number of carbon atoms of the sodium metal salt of the fatty acid or the predetermined number of carbon atoms of the sodium salt of the lower alkyl carboxylic acid.

2. The method as in claim 1, wherein the hydrocarbon coupled radical product comprises the alkyl radical coupled to the lower alkyl radical.

3. The method as in claim 1, wherein the hydrocarbon coupled radical product comprises the alkyl radical coupled to the hydrogen radical.

4. The method as in claim 1, further comprising the step of extracting the lipid from the biomass.

5. The method as in claim 1, wherein the step of converting the lipid into the fatty acid comprises fermentation.

6. The method as in claim 1, wherein the biomass further comprises a carbohydrate that is hydrolyzed to produce a carboxylic acid.

7. The method as in claim 1, wherein a reaction at the cathode in the catholyte compartment produces hydrogen gas and the base from the catholyte.

8. The method as in claim 7, wherein the base produced from the catholyte is reacted with the quantity of biomass to produce the sodium metal salt of a fatty acid.

9. The method as in claim 1, wherein the catholyte comprises a solvent or a mixture of solvents which are different solvents compared to the at least one G-type solvent and at least one H-type solvent included in the anolyte.

10. The method as in claim 1, wherein the G-type solvent comprises a solvent chosen from ethylene glycol, glycerine, 1,2-dihydroxy-4-oxadodecane, 2-methyl-2-propyl-1,3-propanediol, 2-ethyl-1,3-hexanediol, 2-amino-2-methyl-1,3-propanediol, 2,3-butanediol, 3-amino-1,2-propanediol, 1,2-octanediol, cis-1,2-cyclohexanediol, trans-1,2-cyclohexanediol, cis-1,2-cyclopentanediol, 1,2-pentanediol, and 1,2-hexanediol.

11. The method as in claim 1, wherein the H-type solvent comprises a solvent chosen from isopropanol, methanol, ethanol, butanol, amyl alcohol, octanol, hexane, trichloroethane, dichloroethane, methylene, dichloride, chloroform, carbon tetrachloride, tetralin, decalin, monoglyme, diglyme, tetraglyme, acetone, and acetaldehyde.

12. The method as in claim 1, wherein the H-type solvent comprises a recycled fraction of the hydrocarbon coupled radical product of the decarboxylation.

13. The method as in claim 1, wherein the anolyte is at a higher temperature and/or pressure than the catholyte.

14. The method as in claim 1, wherein the sodium salt of a lower alkyl carboxylic acid in the supporting electrolyte comprises sodium acetate.

15. The method as in claim 14, wherein the decarboxylating step forms methyl radicals in addition to the alkyl radicals.

16. The method as in claim 15, wherein hydrogen radicals are formed from photolysis of hydrogen gas added to the anolyte compartment.

17. The method as in claim 1, wherein the sodium salt of a lower alkyl carboxylic acid in the supporting electrolyte comprises sodium formate and wherein the decarboxylating step forms hydrogen radicals from the sodium formate.

18. The method as in claim 1, wherein the step of decarboxylating the sodium metal salt of the fatty acid comprises photolysis.

19. The method as in claim 1, wherein the anode comprises a metal chosen from palladium, rhodium, nickel, platinum, iridium, and ruthenium.

20. The method as in claim 1, wherein the sodium metal salt of the fatty acid is derived from a monocarboxylic acid, a dicarboxylic acid, or a polycarboxylic acid.

21. The method as in claim 1, wherein the biomass further comprises carbohydrates, carboxylic acids, esters of carboxylic acids, triglycerides, oils, phospholipids, carboxylic acid derivatives, lignins, tall oil, resins, switch grass, algae, and/or metal salts of carboxylic acids.

22. The method as in claim 1, wherein the supporting electrolyte is a sodium salt of a lower alkyl carboxylic acid having from one to five carbon atoms.

23. The method as in claim 1, wherein the hydrocarbon coupled radical product comprises a mixture of different hydrocarbons.

24. The method as in claim 1, wherein the number of carbon atoms of the sodium metal salt of the fatty acid and the sodium salt of the lower alkyl carboxylic acid selected to have a predetermined number of carbon atoms are each selected to produce the hydrocarbon coupled radical product comprising a hydrocarbon further comprising a desired total number of carbon atoms.

25. The method as in claim 1, wherein the anolyte further comprises an ionic liquid.

* * * * *